United States Patent [19]

Chene et al.

[11] Patent Number: 5,663,119
[45] Date of Patent: Sep. 2, 1997

[54] PHENYLPYRAZOLE FUNGICIDES

[75] Inventors: Alain Chene, Lyons; Raymond Peignier, Caluire; Jean-Pierre A. Vors, Lyons; Jacques Mortier, Lyons; Richard Cantegril, Lyons; Denis Croisat, Lyons, all of France

[73] Assignee: Rhone-Poulenc Agrochimie, Lyon Cedex, France

[21] Appl. No.: 470,591

[22] Filed: Jun. 7, 1995

Related U.S. Application Data

[62] Division of Ser. No. 959,131, Oct. 9, 1992.

[30] Foreign Application Priority Data

Oct. 9, 1991 [FR] France .................. 91 12647

[51] Int. Cl.$^6$ .................. A01N 43/56
[52] U.S. Cl. .................. 504/280; 548/356.1
[58] Field of Search .................. 548/356.1; 504/280

[56] References Cited

U.S. PATENT DOCUMENTS

| | | |
|---|---|---|
| 2,721,143 | 10/1955 | Kraft et al. . |
| 4,537,617 | 8/1985 | Plath et al. .................. 71/92 |
| 4,792,565 | 12/1988 | Shimotori et al. .................. 514/406 |
| 4,843,068 | 6/1989 | Hamaguchi et al. .................. 514/63 |
| 4,980,345 | 12/1990 | Meki et al. .................. 514/63 |

FOREIGN PATENT DOCUMENTS 637142 5/1993 Australia .

OTHER PUBLICATIONS

Nawrot–Modranka et al, Polish Journal of Chemistry, 62, 417–426 (1988).

Primary Examiner—Gary Geist
Assistant Examiner—Sreeni Padmanabhan
Attorney, Agent, or Firm—Burns, Doane, Swecker & Mathis, L.L.P.

[57] ABSTRACT

Phenylpyrazoles of the formula:

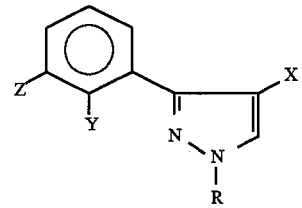

I

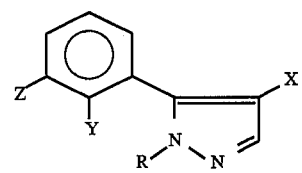

Ia in which:

X=H, hal, $NO_2$, CN, SCN, alkyl ($C_1$–$C_4$), alkenyl ($C_2$–$C_4$), alkynyl ($C_2$–$C_4$), alkoxy ($C_1$–$C_4$), alkylthio ($C_1$–$C_4$), phenyl, phenoxy; mono- or di- alkyl- or phenyl- amino; alkylcarbonyl, carbamoyl, carboxyl, benzoyl; alkyl- sulphinyl or sulphonyl;

Y, Z=H, hal, OH, $NO_2$, NO, CN, SCN, alkyl ($C_1$–$C_4$), alkenyl ($C_2$–$C_4$), alkynyl ($C_2$–$C_4$), alkoxy ($C_1$–$C_4$), alkylthio ($C_1$–$C_4$), phenyl, phenoxy; mono- or di- alkyl- or phenyl- amino; alkylcarbonyl, carbamoyl, carboxyl, benzoyl; alkyl-sulphinyl or sulphonyl, for example; and Y, Z may also form a bridge of 1 to 4 atoms, of which at least one can be a hetero atom, optionally substituted. The products are useful as fungicides in agriculture.

16 Claims, No Drawings

PHENYLPYRAZOLE FUNGICIDES

This application is a divisional of application Ser. No. 07/959,131, filed Oct. 9, 1992.

The present invention relates to new derivatives of the 3-phenylpyrazole family, to processes for their preparation, to the compositions which contain them and to their use for the protection of plants against fungal diseases.

More especially, the subject of the invention is 3-phenylpyrazole derivatives, characterised in that they are of formulae:

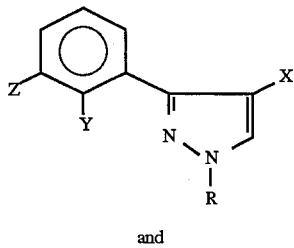

I and

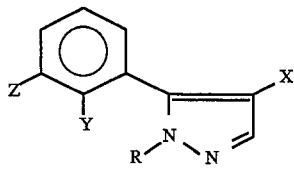

Ia in which:

X is:
  a hydrogen or halogen atom,
  a nitro, cyano or thiocyanato group,
  an alkyl, alkenyl alkynyl, alkoxy or alkylthio group, each of these groups being halogenated or nonhalogenated,
  a phenyl or phenoxy group, each of these groups being optionally substituted by $C_1$–$C_3$ alkyl, $C_1$–$C_3$ haloalkyl or $C_1$–$C_3$ alkoxy,
  an amino substituted or unsubstituted by one or two alkyls or phenyls,
  an alkylcarbonyl, carbamoyl, carboxyl or benzoyl group,
  an alkylsulphinyl or alkylsulphonyl group, it being understood that the alkyl part of all the above groups comprises 1 to 4 carbon atoms unless otherwise defined, and the alkenyl and alkynyl groups contain 2 to 4 carbon atoms;

Y and Z, which are identical or different, are:
  a hydrogen atom, but not together, or halogen atom, a hydroxyl, nitro, nitroso, cyano or thiocyanato group, or an amino substituted or unsubstituted by one or two alkyls or phenyls,
  an alkyl, alkoxy or alkylthio, hydroxyalkyl, alkenyl, alkynyl, alkylsulphinyl or alkylsulphonyl group, the alkyl part of these groups comprising 1 to 4 carbon atoms and being able to be halogenated;
  phenyl, phenyloxy or phenylthio or benzyl, substituted or unsubstituted on the nucleus by $C_1$–$C_3$ alkyl, $C_1$–$C_3$ haloalkyl or $C_1$–$C_3$ alkoxy,
  a formyl, acetyl, alkyl- or alkoxy(thio)carbonyl, mono- or dialkylaminocarbonyl or mono- or dialkylaminothiocarbonyl, carboxyl, carboxylate or carbamoyl group, the alkyl part of these groups comprising 1 to 4 carbon atoms and being able to be substituted by at least one halogen atom,
  or benzoyl, substituted or unsubstituted on the nucleus by $C_1$–$C_3$ alkyl, $C_1$–$C_3$ haloalkyl or $C_1$–$C_3$ alkoxy;

Y and Z can also be joined together via a carbon bridge comprising 1 to 4 atoms, at least one of which can be replaced by an oxygen, sulphur or nitrogen atom, it being possible for the carbons of this bridge to additionally be substituted or unsubstituted by at least one halogen atom and/or at least one alkyl, alkoxy or alkylthio group as defined above, and it being possible for each to be also joined, via a double bond, to an oxygen atom;

R is:
  a) hydrogen, nitro, amino, hydroxyl, cyano, alkyl or haloalkyl, each comprising 1 to 6 carbon atoms, or a phenyl substituted or unsubstituted by at least one halogen atom, one nitro group or haloalkyl containing 1 to 3 carbon atoms;
  b) a group $S(O)_m$—$R_1$, in which:
    m is an integer equal to zero or two, and
    $R_1$ is:
      either, when m is equal to zero:
        a haloalkyl group containing 1 to 6 carbon atoms,
        a phenyl or 3-pyridyl, it being possible for each to be substituted by at least one halogen atom or one nitro, alkyl, haloalkyl, alkoxy or haloalkoxy group, the alkyl part of these four groups comprising 1 to 4 carbon atoms;
      or, when m is equal to two:
        an alkyl or alkoxy group, each comprising 1 to 6 carbon atoms and being substituted or unsubstituted by one or more halogen atoms or alkoxy groups containing 1 to 3 carbon atoms;
        a cycloalkyl group containing 3 to 6 carbon atoms;
        an alkenyl or alkynyl or alkenoxy group, each comprising 3 to 6 carbon atoms;
        a phenyl group, substituted or unsubstituted by 1 to 5 substituents chosen from the group comprising a halogen atom, a nitro group or an alkyl, haloalkyl, alkoxy or haloalkoxy comprising 1 to 4 carbon atoms;
  c) a group $CH_2$—$NR_2R_3$, in which:
    $R_2$ is:
      alkyl containing 1 to 6 carbon atoms, optionally substituted by a substituent chosen from the group comprising cyano, alkoxy, cycloalkyl containing 3 to 7 carbon atoms, alkylcarbonyl, alkoxycarbonyl, mono- or dialkylaminocarbonyl, alkylsulphinyl, alkylsulphonyl or dialkylamino, the alkyl part of these groups comprising 1 to 6 carbon atoms;
      alkenyl or alkynyl containing 2 to 6 carbon atoms;
      cycloalkyl containing 3 to 7 carbon atoms;
      phenyl or benzyl, optionally substituted by a substituent chosen from the group comprising a halogen atom or a cyano, alkyl, alkoxy, haloalkyl or haloalkoxy containing 1 to 9 halogen atoms, alkylcarbonyl or alkoxycarbonyl group, the alkyl part of these groups comprising 1 to 6 carbon atoms;
    $R_3$ is a group:
      Het, Het-alkyl(containing 1 to 6 carbon atoms), or Het-alkenyl or Het-alkynyl(each containing 3 to 6 carbon atoms), optionally substituted by a substituent chosen from the group comprising a halogen atom or a cyano, alkyl, alkoxy, haloalkyl or haloalkoxy containing 1 to 9 halogen atoms, alkylcarbonyl or alkoxycarbonyl group, the alkyl part of these groups comprising 1 to 6 carbon atoms;
      in which Het is a heterocyclic radical containing 5 to 7 atoms, of which 1 to 3 are heteroatoms (nitrogen, oxygen or sulphur), optionally substituted by a substituted chosen from the group comprising a halogen atom or a cyano, alkyl, alkoxy, haloalkyl or haloalkoxy containing 1 to 9 halogen atoms alkylcarbonyl or alkoxycarbonyl group, the alkyl part of these groups comprising 1 to 6 carbon atoms;

dialkylaminoalkyl, the alkyl part of these groups comprising 1 to 6 carbon atoms; cycloalkyl or cycloalkylalkyl (alkyl containing 1 to 4 carbon at&ms) containing 3 to 7 carbon atoms; or phenethyl, optionally substituted by a substituent chosen from the group comprising a halogen atom, a cyano group, or an alkyl or alkoxy group each containing 1 to 4 carbon atoms;

$R_2$ and $R_3$ can additionally form, with the nitrogen atom to which they are joined, a nitrogen-containing ring containing 6 atoms, 4 of which are carbon atoms, optionally substituted, and the fifth is a carbon atom or a heteroatom such as oxygen, sulphur or nitrogen which can be substituted by an alkyl group containing 1 to 6 carbon atoms, it being possible for the nitrogen-containing ring itself to be substituted by one or two substituents chosen from the group comprising cyano, alkylcarbonyl, alkoxycarbonyl, mono- or dialkylaminocarbonyl, alkylsulphinyl or alkylsulphonyl, the alkyl part of these groups comprising 1 to 6 carbon atoms, or phenylsulphinyl or phenylsulphonyl;

d) a group $(CH_2)_m$—$R_4$, in which:
  m is equal to 1 or 2,
  $R_4$ is a cyano, nitro, alkylcarbonyl, phenylcarbonyl, alkoxycarbonyl, mono- or dialkylaminocarbonyl, $P(O)(alkoxy)_2$, $P(O)(benzyloxy)_2$, $P(O)(phenoxy)_2$, trialkylsilyl or phenyl group, it being understood that the alkyl radical of these groups comprises 1 to 4 carbon atoms and is optionally halogenated and that the phenyl nucleus of the aromatic radicals can be substituted by 1 to 5 substituents chosen from the group comprising a halogen atom, a nitro group or an alkyl, alkoxy, haloalkyl, haloalkoxy or alkoxycarbonyl radical, the alkyl part of each of these radicals comprising 1 to 4 carbon atoms;

e) a group $CH(R_5)$—X—$R_6$, in which:
  $R_5$ is a hydrogen atom or an alkyl containing 1 to 4 carbon atoms,
  X is an oxygen atom or a group $S(O)_n$, in which:
    n is an integer equal to zero or two,
  $R_6$ is:
    alkyl containing 1 to 4 carbon atoms, optionally substituted by a substituent chosen from the group comprising a halogen atom or a cyano, alkoxy, phenoxy, benzyloxy or trialkylsilyl group, the alkyl part of each of these radicals comprising 1 to 4 carbon atoms and the phenyl nuclei being able to be substituted by 1 to 5 substituents chosen from the group comprising a halogen atom, a nitro group or an alkyl, alkoxy, haloalkyl or haloalkoxy radical, the alkyl part of each of these radicals comprising 1 to 4 carbon atoms;
    alkenyl or alkynyl containing 3 to 6 carbon atoms;
    phenyl or benzyl, which can be substituted by 1 to 5 substituents chosen from the group comprising a halogen atom, a nitro-group or an alkyl, alkoxy, haloalkyl or haloalkoxy radical (1 to 4 carbon atoms);

f) a group $CHR_7R_8$, in which:
  $R_7$ is a hydrogen atom or a haloalkyl or alkoxy group, each containing 1 to 4 carbon atoms,
  $R_8$ is a halogen atom or a hydroxyl, alkoxy or O—C$(O)R_9$ group with
    $R_9$ being a hydrogen atom, an alkyl, haloalkyl or alkenyl containing 1 to 4 carbon atoms, tetrahydrofuryl, tetrahydropyranyl or alkoxycarbonyl group, the alkyl part of each of these radicals comprising 1 to 6 carbon atoms;

g) a group $C(X)$—$R_{10}$, in which:
  X is an oxygen or sulphur atom,
  $R_{10}$ is:
    a hydrogen or halogen atom,
    an alkyl group containing 1 to 6 carbon atoms, optionally substituted by a substituent chosen from the group comprising a halogen atom or a cyano, nitro, alkylcarbonyl, alkoxycarbonyl or mono- or dialkylaminocarbonyl group, the alkyl part of each of these radicals comprising 1 to 4 carbon atoms, or a cycloalkyl group containing 3 to 6 carbon atoms;
    an alkenyl or alkynyl group, containing 3 to 6 carbon atoms, optionally substituted by a phenyl which can be substituted by 1 to 5 substituents chosen from the group comprising a halogen atom, a nitro group or an alkyl, alkoxy, haloalkyl or haloalkoxy radical, the alkyl part of each of these radicals comprising 1 to 4 carbon atoms;
    a phenyl, benzyl, 2-pyridyl, 3-pyridyl or 4-pyridyl group, it being possible for the nuclei to be substituted by 1 to 5 substituents chosen from the group comprising a halogen atom, a nitro or cyano group, or an alkyl, alkoxy, haloalkyl, haloalkoxy, alkylcarbonyl or alkoxycarbonyl radical, the alkyl part of each of these radicals comprising 1 to 4 carbon atoms;

a group $CH(R_{11})$—X—$R_{12}$, in which:
  $R_{11}$ is a hydrogen atom or an alkyl containing 1 to 4 carbon atoms,
  X is an oxygen atom or the group $S(O)_p$, with p equal to zero or 2;
  $R_{12}$ is an alkyl containing 1 to 4 carbon atoms, optionally substituted by a halogen atom or an alkoxy containing 1 to 4 carbon atoms; an alkenyl or alkynyl group, containing 3 to 6 carbon atoms; a phenyl or benzyl group which can be substituted by 1 to 5 substituents chosen from the group comprising a halogen atom, a nitro group or an alkyl, alkoxy, haloalkyl or haloalkoxy radcial (1 to 4 carbon atoms);

a group $CH(R_{11})$—$NR_{13}R_{14}$, in which $R_{13}$ and $R_{14}$, which are identical or different, are each:
  an alkyl containing 1 to 4 carbon atoms, optionally substituted by a cyano, alkylcarbonyl, alkoxycarbonyl or dialkylaminocarbonyl group, halogen atom or an alkoxy containing 1 to 4 carbon atoms;
  a phenyl or benzyl group which can be substituted by 1 to 5 substituents chosen from the group comprising a halogen atom, a nitro or cyano group or an alkyl, alkoxy, haloalkyl, haloalkoxy or alkoxycarbonyl radical, the alkyl part of each of these radicals comprising 1 to 4 carbon atoms;

a group $CHR_{11}$—$R_{15}$, in which:
  $R_{11}$ is as defined above and
  $R_{15}$ is a heterocyclic group $NC_4R_{16}R_{17}T$, in which $R_{16}$ and $R_{17}$, which are identical or different, are a hydrogen atom or an alkyl or alkoxycarbonyl group, each containing 1 to 3 carbon atoms, and T is an oxygen or sulphur atom, or a carbonyl or N—$R_{18}$ group, in which $R_{18}$, is a hydrogen atom or an alkyl formyl, alkylcarbonyl or alkoxycarbonyl group, the alkyl part of each of these radicals comprising 1 to 4 carbon atoms;

h) a group —C(O)—X—$R_{19}$, in which:

X is an oxygen or sulphur atom, $R_{19}$ is:

an alkyl group containing 1 to 6 carbon atoms, optionally substituted by a substituent chosen from the group comprising a halogen atom or a cyano group; a cycloalkyl group containing 3 to 6 carbon atoms, optionally substituted by an alkyl containing 1 to 3 carbon atoms; trialkylsilyl, phenylsulphonyl, optionally substituted by at least one halogen atom or an alkyl group; alkoxycarbonyl or dialkylaminocarbonyl; the alkyl part of each of the above radicals comprising 1 to 4 carbon atoms;

an alkenyl or alkynyl group containing 2 to 6 carbon atoms, optionally substituted by a phenyl which can be substituted by 1 to 5 substituents chosen from the group comprising a halogen atom, a nitro group or an alkyl radical;

a phenyl, benzyl, 2-pyridyl, 3-pyridyl or 4-pyridyl group, it being possible for the nuclei to be substituted by 1 to 5 substituents chosen from the group comprising a halogen atom, a nitro or cyano group, or an alkyl, alkoxy, haloalkyl, haloalkoxy, alkylcarbonyl or alkoxycarbonyl, alkylthio, alkylsulphinyl or alkylsulphonyl radical, the alkyl part of each of these radicals comprising 1 to 4 carbon atoms;

a phenylalkyl group or a heterocyclylalkyl group, in which the alkyl part comprises 1 to 4 carbon atoms and the heterocyclyl part can be 2-pyridyl, 3-pyridyl, 4-pyridyl, 2- furyl, 3-furyl, 2-thienyl or 3-thienyl, it being possible for the nuclei to be substituted by 1 to 5 substituents chosen from the group comprising a halogen atom a nitro group, or an alkyl alkoxy, haloalkyl, haloalkoxy, alkylcarbonyl or alkoxycarbonyl, alkylthio, alkylsulphinyl or alkylsulphonyl radical;

i) a group C(X)—$NR_{20}R_{21}$, in which:

X is an oxygen or sulphur atom, $R_{20}$ and $R_{21}$ are each:

a hydrogen atom or an alkyl group containing 1 to 4 carbon atoms, optionally substituted by a substituent chosen from the group comprising a halogen atom or a cyano, alkylcarbonyl, alkoxycarbonyl or dialkylaminocarbonyl group, the alkyl part of each of the above radicals comprising 1 to 4 carbon atoms;

a cycloalkyl group containing 3 to 6 carbon atoms, optionally substituted by an alkyl containing 1 to 3 carbon atoms, an alkenyl or alkynyl group containing 3 to 6 carbon atoms, a phenyl or benzyl group, it being possible for the nuclei of each to substituted by 1 to 5 substituents chosen from the group comprising a halogen atom, a nitro or cyano group, or an alkyl, alkoxy, haloalkyl, haloalkoxy, alkylcarbonyl or alkoxycarbonyl, alkylthio, alkylsulphinyl or alkylsulphonyl radical, the alkyl part of each of these radicals comprising 1 to 4 carbon atoms;

$R_{20}$ and $R_{21}$ can additionally form, with the nitrogen atom to which they are joined, a ring containing 6 atoms, 4 of which are optionally substituted carbon atoms and the fifth of which is a carbon atom or a heteroatom such as oxygen, sulphur or nitrogen;

j) a group $SiR_{22}R_{23}R_{24}$, in which $R_{22}$, $R_{23}$ and $R_{24}$, which are identical or different, are each an alkyl group containing 1 to 4 carbon atoms, or a phenyl or benzyl group, k) a group $P(X)R_{25}R_{26}$, in which:

X is an oxygen or sulphur atom, $R_{25}$ and $R_{26}$, which are identical or different, are each an alkyl or alkoxy group containing 1 to 4 carbon atoms, or a phenyl, phenoxy, benzyl or benzoxy group.

In the formula, X is preferably a chlorine or bromine atom.

Other preferred derivatives are such that, in the formulae I and Ia, Y and/or Z are a hydrogen or chlorine atom.

Other preferred derivatives are such that, in the formulae I and Ia, Y and Z together form a bridge comprising 3 or 4 atoms.

Other preferred derivatives are such that, in the formulae I and Ia, Y and Z form an optionally halogenated methylenedioxy bridge.

Other preferred derivatives are such that, in the formulae I and Ia, R is an alkyl(1 to 3 carbon atoms)carbonyl, alkoxy(1 to 3 carbon atoms)carbonyl, phenylcarbonyl or phenoxycarbonyl.

The derivatives according to the invention can be prepared by various processes known per se, especially in the compilations "Comprehensive Heterocyclic Chemistry", A. R. Katritzky and C. W. Rees, 1984, Vol. 5, pages 239 to 241 and 263, Pergamon Press; "Advances in Heterocyclic Chemistry", A. N. Kost and I. I. Grandberg, 1966, Vol. 6, pages 391 to 396, Academic Press and "The Chemistry of Heterocyclic Compounds", L. C. Behr, R. Fusco and C. H. Jardoe, 1967, J. Wiley & Sons.

A first process consists in reacting a 3-phenylpyrazole of formula II, in which Y and Z have the same meaning as in the formula I, with a halogenating agent.

As halogenating agent, there may be mentioned, as chlorinating agent, chlorine, preferably in aqueous medium, such as in water, or in an organic medium such as acetic acid or carbon tetrachloride, or else hypochlorous acid, hydrochloric acid in the presence of hydrogen peroxide in acetic acid, or else sulphuryl chloride or an N-chloroimide, such as N-chlorosuccinimide, in a chlorinated solvent such as dichloromethane or else phosphorus pentachloride.

Chlorination can be carried out with chlorine in organic solvent medium, preferably a lower carboxylic acid, at a temperature from 16° to 30° C., preferably at room temperature, the tea&rants being in a substantially stoichiometric molar ratio. Chlorination can also be carried out with N-chlorosuccinimide in organic solvent medium, preferably a chlorinated solvent such as dichloromethane or 1,2-dichloroethane, at a temperature of 0° C. to 80° C. and preferably from 20° C. to 50° C., the reactants being in a substantially stoichiometric molar ratio.

There may be cited, as brominating agent, bromine, preferably in an aqueous solvent such as water, in acidic medium, for example nitric or acetic acid, in the presence or absence of a base such as sodium acetate, or in an organic solvent, such as, for example, chloroform, or else pyridinium perbromide.

Bromination can be carried out, for example, with bromine in organic solvent medium such as a lower carboxylic acid, at a temperature of 16° C. and preferably at room temperature.

There can be used, as iodinating agent, iodine in the presence of hypoiodous acid or in the presence of a base such as an alkali metal hydroxide or a basic salt such as sodium acetate, or in the presence of a nickel(II) salt. It is also possible to use iodine with the silver(I) salt of the pyrazole of formula I. It is also possible to use N-iodosuccinimide, as indicated above for N-chlorosuccinimide.

Fluorination can be carried out from derivatives of formula V, in which Y and Z have the same meaning as in the formula I by preparation of the diazonium tetrafluoroborate derivative derived from the 4-amino group and then by irradiation of this compound.

A second process known per se for the preparation of the derivatives of formula I according to the invention consists in reacting a 4-formyl-3-phenylpyrazole of formula IV with bromine in acetic acid to give 4-bromo-3-phenylpyrazole.

The compounds of formula II can be prepared, in a very known per se, by reaction with hydrazine of a derivative of formula III, in which X is a hydrogen atom and W is a hydroxyl radical or a chlorine atom and Y and Z have the same meanings as in the formula I.

It is also possible to prepare, in a way known per se, the derivatives of formula II from derivatives of formula III, in which X is a hydrogen atom and W a dialkylamino group, Y and Z being defined as above, by reaction with hydrazine hydrate at a temperature of 10° C. to 150° C., preferably from 60° C. to 120° C., advantageously in organic solvent medium, preferably a lower carboxylic acid or in an alcohol in the presence of an organic or inorganic acidic catalyst, the molar ratio of the 2 reactants being substantially stoichiometric.

The derivatives of formula III, in which X is a hydrogen atom and W a dialkylamino group, Y and Z being defined as above, can be obtained, in a way known per se, by reaction of acetophenones of formula VI, in which Y and Z are defined as above, with amide acetals, ester aminals or orthoaminals, preferably in the absence of organic solvent with dialkyl (preferably dimethyl or diethyl) acetals of N,N-dimethylformamide, at a temperature of 20° C. to 130° C. and preferably from 70° C. to 130° C.

The following examples are given in order to illustrate the preparation and the fungicidal activity of the derivatives according to the invention. The structure of the latter was Confirmed by NMR analysis.

EXAMPLE 1

25 g (0.162 mol) of 2'-chloroacetophenone are dissolved, at room temperature and with stirring, in 60 ml of N,N-dimethylformamide dimethyl acetal. Stirring is maintained and the reaction mixture is heated for 4 h 30 at 80° C. The mixture is concentrated to dryness under reduced pressure. The residue is taken up in 150 ml of methylene chloride. The resulting organic solution is washed with water, dried over $MgSO_4$ and then concentrated. The residue is chromatographed on a silica column (eluent: heptane/ethyl acetate 50/50). 27.0 g (0.129 mol) of 1-(2-chlorophenyl)-3-dimethylamino-2-propen-1-one (compound 1) (yield 80%), the structure of which is confirmed by NMR, was obtained in a honey-like consistency.

EXAMPLE 2

By carrying out the preparation as in Example 1 but by using the appropriate reactants, the derivatives of formula III collated in the following Table A were obtained:

| COMPOUND No. | Y | Z | Yield | M.p. (°C.) or analysis |
|---|---|---|---|---|
| 2 | F | H | 66 | NMR |
| 3 | H | Cl | 63 | 72 |
| 4 | Cl | Cl | 87 | 89 |
| 5* | $OCF_2$ | O | 76 | 84 |
| 6 | $SCH_3$ | H | 95 | NMR |
| 7 | $CH_3$ | H | 69 | NMR |
| 8 | H | $CH_3$ | 73 | 45 |
| 27 | $nC_3H_7$ | Cl | 100 | NMR |
| 28 | $CH_3$ | $CF_3$ | 100 | NMR |
| 29 | H | $OCF_3$ | 95 | NMR |
| 30 | $OCH_3$ | Cl | 97 | NMR |
| 31 | Cl | Br | 91 | 114 |
| 32 | H | $CF_3$ | 79 | 62 |
| 33 | $C_2H_5$ | Cl | 80 | 94 |
| 34 | F | Br | 75 | 54 |
| 35 | H | CN | 93 | 118 |
| 36 | $O(CH_2)_2$ | O | 65 | NMR |
| 37 | $SOCH_3$ | Cl | 93 | 102 |
| 38 | Cl | F | 88 | 72 |
| 39 | $CH_3$ | Cl | 84 | 76 |
| 40 | F | Cl | 83 | 64 |
| 41 | $OCH_2$ | O | 57 | 118 |
| 42 | F | $CF_3$ | 72 | 59 |
| 43 | $OCH_3$ | $OCH_3$ | 83 | NMR |
| 44 | F | F | 79 | 62 |
| 45 | $CH_3$ | H | 69 | NMR |
| 46 | H | F | 84 | 73 |
| 47 | naphthyl | naphthyl | 100 | oil |
| 48 | $NO_2$ | Cl | 73 | 170 |
| 49 | $C_6H_5CH_2O$ | H | 68 | 75 |
| 50 | $CH_3$ | $CH_3$ | 65 | solid |
| 51 | Cl | $NO_2$ | 73 | 116 |
| 52 | H | $NO_2$ | 67 | 105 |
| 53 | $NO_2$ | H | 80 | 132 |
| 54 | H | Br | 89 | oil |
| 55 | $(CH_3)_3SiCH_2$ | Cl | 83 | honey |
| 56 | Br | H | 99 | oil |
| 57 | $CF_3$ | H | 98 | oil |
| 58 | $NO_2$ | $CH_3$ | 95 | 161 |
| 59 | $C_2H_5O$ | Cl | 100 | honey |

*Here and throughout these Examples, where Y is indicated as $OCF_2$ and Z as O, Y and Z are joined to form a —$OCF_2O$— radical, and analogously for Y=$O(CH_2)_2$ and Z=O, and so forth.

EXAMPLE 3

7 g (0.0540 mol) of hydrazine hydrate are added, slowly and at room temperature, to a solution of 10.5 g (0.050 mol) of 1-(2-chlorophenyl)-3-dimethylamino-2-propen-1-one, prepared in Example 1, in 60 ml of ethanol. The reaction mixture is stirred for 5 hours at room temperature then left standing for 12 hours before being concentrated to dryness. The residue is recrystallised from a heptane/ethyl acetate mixture. 6.9 g (0.0386 mol) of 3-(2'-chlorophenyl)-1H-pyrazole are obtained, which melts at 93° C. (yield 77%) (compound 60).

EXAMPLE 4

By carrying out the preparation as in Example 3 but by using the appropriate reactants, the derivatives of formula II, collated in the following Table B, were obtained:

| COMPOUND No. | Y | Z | Yield | M.p. (°C.) or analysis |
|---|---|---|---|---|
| 10 | F | H | 73 | 51 |
| 11 | H | Cl | 96 | 84 |
| 12 | Cl | Cl | 90 | 121 |
| 13 | OCF$_2$ | O | 80 | 130 |
| 14 | SCH$_3$ | H | 53 | 90 |
| 15 | CH$_3$ | H | 92 | NMR |
| 16 | H | CH$_3$ | 61 | NMR |
| 61 | nC$_3$H$_7$ | Cl | 41 | NMR |
| 62 | H | OCF$_3$ | 87 | 98 |
| 63 | OCH$_3$ | Cl | 94 | 100 |
| 64 | Cl | Br | 50 | 160 |
| 65 | H | CF$_3$ | 86 | 67 |
| 66 | C$_2$H$_5$ | Cl | 63 | 77 |
| 67 | F | Br | 75 | 121 |
| 68 | H | CN | 90 | 85 |
| 69 | CF$_3$ | H | 67 | 73 |
| 70 | SOCH$_3$ | Cl | 86 | 168 |
| 71 | Cl | F | 100 | 120 |
| 72 | CH$_3$ | Cl | 87 | 74 |
| 73 | F | Cl | 81 | 103 |
| 74 | OCH$_2$ | O | 91 | 50 |
| 75 | F | CF$_3$ | 90 | 86 |
| 76 | OCH$_3$ | OCH$_3$ | 86 | 90 |
| 77 | F | F | 86 | 90 |
| 78 | CH$_3$ | H | 93 | NMR |
| 79 | H | F | 76 | 77 |
| 80 | naphthyl | naphthyl | 81 | 119 |
| 81 | NO$_2$ | Cl | 46 | 173 |
| 82 | C$_6$H$_5$CH$_2$O | H | 83 | 62 |
| 83 | CH$_3$ | CH$_3$ | 66 | 79 |
| 84 | Cl | NO$_2$ | 93 | 117 |
| 85 | H | NO$_2$ | 70 | 126 |
| 86 | NO$_2$ | H | 95 | 80 |
| 87 | H | Br | 89 | 106 |
| 88 | (CH$_3$)$_3$SiCH$_2$ | Cl | 56 | honey |
| 89 | Br | H | 72 | 134 |
| 90 | CF$_3$ | H | 67 | 72 |
| 91 | NO$_2$ | CH$_3$ | 81 | 137 |
| 92 | NO$_2$ | SC$_6$H$_5$ | 8 | 164 |
| 93 | C$_2$H$_5$O | Cl | | 96 |

EXAMPLE 5

3.5 g of 3-(2-chlorophenyl)-1H-pyrazole, prepared as in Example 9, are dissolved, at room temperature and with stirring, in 20 ml of acetic acid. A solution of 3.76 g (0.0235 mol) of bromine in 20 ml of acetic acid is then run dropwise into the reaction mixture. Stirring is maintained for 1 hour at room temperature and then the acetic acid and the excess bromine are driven off under reduced pressure. The residue is taken up in methylene chloride and this organic solution is washed with an aqueous bicarbonate solution, then with water and then dried over MgSO$_4$ before being concentrated to dryness. The residue is recrystallised from pentane. 3.3 g (0.0128 mol) of 3-(2'-chlorophenyl)-4-bromo-1H-pyrazole are obtained, which melts at 80° C. (yield 65%) (compound 94)

EXAMPLE 6

By carrying out the preparation as in Example 5 but by using the appropriate reactants, the derivatives of formula I, in which X is a bromine atom, collated in the following Table C, were obtained:

| COMPOUND No. | Y | Z | Yield % | M.p. (°C.) or analysis |
|---|---|---|---|---|
| 18 | F | H | 54 | NMR |
| 19 | H | Cl | 95 | 119 |
| 20 | Cl | Cl | 86 | 140 |
| 21 | OCF$_2$ | O | 50 | 144 |
| 95 | NO$_2$ | Cl | 44 | 190 |

EXAMPLE 7

6.8 g (0.038 mol) of 3-(2'-chlorophenyl)-1H-pyrazole, prepared as in Example 9, are dissolved, at temperature and with stirring, in 30 ml of acetic acid. 2.9 g (0.0409 mol) of chlorine are then introduced into the reaction mixture. Stirring is maintained for 1 hour at room temperature and then the acetic acid is driven off under reduced pressure. The residue is taken up in methylene chloride and this organic solution is washed with in aqueous bicarbonate solution, then with water and then dried over Na$_2$SO$_4$ before being concentrated to dryness. The residue is chromatographed on a silica column (eluent: heptane/ethyl acetate 60/40). 3.6 g of 3-(2'-chlorophenyl)-4-chloro-1H-pyrazole (compound 96) are obtained, which is of honey-like consistency (yield 44%).

EXAMPLE 8

2.3 g (0.015 mol) of 3-(3-methylphenyl)-1H-pyrazole are dissolved in 45 ml of dichloromethane at room temperature and with stirring. 2.1 g (0.016 mol) of N-chlorosuccinimide are then added and stirring is then continued for 60 hours at room temperature. The reaction mixture is then concentrated and then chromatographed on a silica column (eluent: heptane/ethyl acetate 80/20). 1.4 g (0.007 mol) of 4-chloro-3-(3-methylphenyl)-1H-pyrazole (compound 97) is obtained which melts at 109° C. (yield 50%).

EXAMPLE 9

By carrying out the preparation as in Example 8, using the appropriate reactants, the derivatives of formula I in which X is a chlorine atom, collated in the following Table D, were obtained:

| COMPOUND No. | Y | Z | Yield % | M.p. (°C.) or analysis |
|---|---|---|---|---|
| 24 | Cl | Cl | 53 | 140 |
| 25 | OCF$_2$ | O | 40 | 147 |
| 26 | CH$_3$ | H | 88 | NMR |
| 98 | nC$_3$H$_7$ | Cl | 47 | NMR |
| 99 | CH$_3$ | CF$_3$ | 68 | NMR |
| 100 | H | OCF$_3$ | 54 | 62 |
| 101 | OCH$_3$ | Cl | 44 | 70 |
| 102 | Cl | Br | 65 | 142 |
| 103 | H | CF$_3$ | 100 | 81 |
| 104 | C$_2$H$_5$ | Cl | 83 | 84 |
| 105 | F | Br | 88 | 114 |
| 106 | H | CN | 79 | 110 |
| 107 | O(CH$_2$)$_2$ | O | 74 | NMR |
| 108 | CF$_3$ | H | 40 | 111 |
| 109 | SOCH$_3$ | Cl | 41 | 171 |
| 110 | Cl | F | 94 | 105 |
| 111 | CH$_3$ | Cl | 28 | NMR |
| 112 | F | Cl | 46 | 120 |
| 113 | OCH$_2$ | O | 85 | 100 |
| 114 | F | CF$_3$ | 67 | 97 |
| 115 | OCH$_3$ | OCH$_3$ | 20 | 90 |

-continued

| COMPOUND No. | Y | Z | Yield % | M.p. (°C.) or analysis |
|---|---|---|---|---|
| 116 | F | F | 68 | 95 |
| 117 | $CH_3$ | H | 88 | NMR |
| 118 | H | F | 57 | 120 |
| 119 | naphthyl | naphthyl | 77 | 170 |
| 120 | $NO_2$ | Cl | 80 | 186 |
| 121 | $C_6H_5CH_2O$ | H | 89 | 91 |
| 122 | $CH_3$ | $CH_3$ | 33 | 89 |
| 123 | H | Cl | 13 | 122 |
| 124 | Cl | $NO_2$ | 70 | 162 |
| 125 | H | $NO_2$ | 85 | 148 |
| 127 | $NO_2$ | H | 91 | honey |
| 128 | H | Br | 80 | 151 |
| 129 | $(CH_3)_3SiCH_2$ | Cl | 87 | 92 |
| 130 | $NO_2$ | $CH_3S$ | 60 | honey |
| 131 | $NO_2$ | $N(CH_3)_2$ | 40 | honey |
| 132 | $NH_2$ | Cl | 71 | 121 |
| 133 | Br | H | 92 | honey |
| 134 | $NO_2$ | $CH_3$ | 46 | 169 |
| 135 | $C_2H_5O$ | Cl |  | 96 |
| 136 | $NO_2$ | $SC_6H_5$ | 8 | 164 |

EXAMPLE 10

4-Iodo-3-(2,2-difluoro-1,3-benzodioxol-4-yl) pyrazole (compound 137)

1.03 g (0.0046 mol) of N-iodosuccinimide are added to a solution of 1 g (0.0045 mol) of the corresponding 4H-pyrazole obtained in Example 13 in 50 ml of dichloroethane. The reaction mixture is stirred for 12 hours at room temperature and then concentrated to dryness. The residue obtained is purified by passing through a silica column with a heptane/ethyl acetate 7/3 mixture as eluent to obtain a white powder, of melting point 142° C., with a yield of 79.5%.

EXAMPLE 11

3-(2-Chlorophenyl)-4-cyanopyrazole 10 g (0.0055 mol) of 2-chlorobenzoylacetonitrile are dissolved at room temperature and with stirring in 30 ml of N,N-dimethylformamide dimethyl acetal according to the procedure described in Example No. 1. 7.5 g (0.032 mol) of the compound thus obtained (3-(2-chlorophenyl)-2-cyano-1-dimethylamino-1-propen-3-one, yield 96%) are dissolved in 80 ml of acetic acid and then 2 ml (0.04 mol) of hydrazine hydrate are added according to the procedure described in Example No. 1. After trituration in heptane, 4.1 g of 3-(2-chlorophenyl)-4-cyanopyrazole (compound 138) are obtained:

Yield 63%, M.p.=160° C.

EXAMPLE 12

4-Ethoxycarbonyl-3-(2-chlorophenyl)pyrazole (compound 139)

2.04 g (0.01 mol) of 3-(2-chlorophenyl)-4-cyanopyrazole, obtained according to Example No. 3, are treated with 2.4 ml of 95% ethanol and 1.1 ml of concentrated $H_2SO_4$ and are maintained at reflux for 6 hours. The reaction mixture is poured into water and then extracted with $CH_2Cl_2$. The organic phase is dried over $MgSO_4$, and then concentrated. The residue obtained is purified by passing through a silica column ($CH_2Cl_2$/MeOH 98/2) to obtain a pale yellow oil:

Yield 36%. NMR analysis No. 42280.

EXAMPLE 13

3-(2-Chlorophenyl)-4-thiocarbamoylpyrazole (compound 140)

1 g (0.005 mol) of 3-(2-chlorophenyl)-4-cyanopyrazole, obtained according to Example 11, and 0.75 g (0.01 mol) of thioacetamide are successively added to a solution of 10 ml of DMF which is saturated with gaseous hydrochloric acid. The reaction mixture is maintained at 100° C. for 2 hours, then cooled to room temperature and poured into water. The reaction mixture is then washed with an aqueous sodium bicarbonate solution and then extracted with $CH_2Cl_2$. After drying the organic phase over $MgSO_4$ and evaporating, the residue obtained is purified by passing through a silica column (heptane/ethyl acetate 1/1) in order to obtain a pale yellow powder:

Yield 36% M.p.=215° C.

EXAMPLE 14

4-Cyano-3-(2,2-difluoro-1,3-benzodioxol-4-yl)-pyrazole (compound 141)

The intermediate 3-oxo-3-(2,2-difluoro-1,3-benzodioxol-4-yl) propanonitrile is obtained according to the method described in Synthesis, 1983, 308 by J. C. Krauss, T. L. Cupps, D. S. Wise and L. B. Townsend by condensation of the anion of cyanoacetic acid with the chloride of (2,2-difluoro-1,3-benzodioxol-4-yl)carboxylic acid obtained according to the procedure described in the patent EP 333658. 5 g (0.022 mol) of 3-oxo-3-(2,2-difluoro-1,3-benzodioxol-4-yl)-propanonitrile are then dissolved in 10 ml of N,N-dimethylformamide dimethyl acetal and the solution is heated at 70° C. The 5.7 g (0.022 mol) of the compound thus obtained (2-cyano-3-(2,2-difluoro-1,3-benzodioxol-4-yl)-1-dimethylamino-1-propen-3-one) are dissolved in 50 ml of acetic acid and then treated with 1.5 ml (0.025 mol) of hydrazine hydrate. After passing through a silica column (heptane/ethyl acetate 6/4), 2.42 g of a pale yellow powder are obtained:

Yield 44% M.p.=175° C.

EXAMPLE 15

3-(2,2-Difluoro-1,3-benzodioxol-4-yl)-4-formylpyrazole (compound 142)

1.1 g (0.0044 mol) of 4-cyano-3-(2,2-difluoro-1,3-benzodioxol-4-yl) pyrazole obtained above in Example No. 14 are dissolved in 10 ml of toluene under a nitrogen atmosphere at −65° C. and 5.74 ml (0.0057 mol) of diisobutylaluminium hydride in solution in toluene are added. After stirring for 30 minutes at −70° C., the reaction mixture is brought progressively to room temperature and then stirred for 3 hours. The reaction mixture is then hydrolysed with a saturated aqueous ammonium chloride solution and then with a 10% aqueous hydrochloric acid solution to a pH of 4. After extracting with ethyl acetate, the organic phase is dried over $MgSO_4$ and evaporated. The oil thus obtained is triturated in a heptane/diisopropyl ether mixture in order to obtain a yellow powder.

Yield 50%. M.p.=115° C.

EXAMPLE 16

3-(2,2-Difluoro-1,3-benzodioxol-4-yl)-4-methylpyrazole (compound 143)

12 g of 1-(2,2-difluoro-1,3-benzodioxol-4-yl)propanone are prepared by condensation-of N,N- dimethylpropionamide with the lithiated anion of 2,2-difluoro-1,3-benzodioxole obtained according to the procedure described in patent EP 333658, are then dissolved in 14.6 ml (0.11 mol) of N,N-dimethylformamide dimethyl acetal and heated at 70° C. according to the procedure described in Example No. 1. 25 g (0.05 mol) of enaminone thus obtained are dissolved in 130 ml of acetic acid and then 3.3 ml (0.069 mol) of hydrazine hydrate are added. The crude product obtained is purified by trituration in pentane.

Yield 27%. M.p.=93° C.

EXAMPLE 17

3-(2,2-Difluoro-1,3-benzodioxol-4-yl)-4-nitropyrazole (compound 144)

6 ml of concentrated sulphuric acid and then, in portions, 1.92 g (0.019 mol) of $KNO_3$ are successively added at 0° C. to a solution of 3 g (0.013 mol) of pyrazole (Y=H), obtained according to Example No. 1 described above, in 60 ml of dichloroethane. The reaction mixture is then stirred at 0° C. for 1 hour, then brought to room temperature and stirred for 40 minutes. The reaction mixture is precipitated by addition of ice and then filtered in order to obtain a beige powder.

Yield 50%. M.p.=135° C.

EXAMPLE 18

3-(2,2-Difluoro-1,3-benzodioxol-4-yl)-4-pyrazolediazonium tetrafluoroborate compound (145)

3-(2,2-Difluoro-1,3-benzodioxol-4-yl)-4-nitropyrazole obtained above in Example 17 is reduced to 4-amino-3-(2,2-difluoro-1,3-benzodioxol-4-yl)pyrazole according to the method described by Vogel (Practical Organic Chemistry, Fourth Edition p. 660: Fe/HCl). 0.8 g (0.003 mol) of 4-amino-3-(2,2-difluoro-1,3-benzodioxol-4-yl)pyrazole in solution in 10 ml of anhydrous THF is treated at 0° C. with a solution of 10 ml of THF containing 1 ml (0.0081 mol) of boron trifluoride etherate 0.6 ml (0.005 mol) of tert-butyl nitrite in solution in 5 ml THF are then added to the reaction mixture. Stirring is maintained for 1 hour at 0° C., the reaction mixture is then diluted with pentane and filtered on a sintered glass. After drying, a beige powder is obtained.

Yield 37%. M.p.=210° C.

EXAMPLE 19

4-Acetyl-3-(2,2-difluoro-1,3-benzodioxol4-yl) pyrazole (compound 146)

8 g (0.04 mol) of 4-acetyl-(2,2-difluoro-1,3-benzodioxole) obtained according to patent EP 333658 in solution in 20 ml of ether are added to a suspension of 3.2 g (0.08 mol) of 60% sodium hydride in 30 ml of ether containing 7 g (0.08 mol) of ethyl acetate. The end of the addition is followed by heating the reaction mixture at reflux for 2 hours. The reaction mixture is diluted with 50 ml of ether and then 2 ml of absolute ethanol and 20 ml of water are added in order to destroy the excess NaH. The pH of the reaction mixture is then brought to 6 by addition of a 1N aqueous hydrochloric acid solution. After extracting with ether, drying over $MgSO_4$, evaporation and purification by passing through a silica column (heptane/ethyl acetate 9/1), 5 g of a pale yellow powder, 1-(2,2-difluoro-1,3-benzodioxol-4-yl)-1,3-butanedione, are obtained.

Yield 52%. M.p.=85° C.).

2.04 g (0.0084 mol) of the latter compound are then dissolved in 1.23 ml (0.0092 mol) of N,N-dimethylformamide dimethyl acetal according to the procedure described in Example No. 1 and heated at 70° C. according to the procedure described in Example No. 1 and then treated, after isolation of the intermediate enaminone, with 0.43 ml (0.0092 mol) of hydrazine hydrate according to the procedure described in Example No. 1. The desired compound is separated from the reaction mixture by silica column chromatography (heptane/ethyl acetate 6/4):

Yield 23%. M.p.=108° C.

EXAMPLE 20

4-Methylthio-3-(2-nitro-3-chlorophenyl)pyrazole (compound 147)

7 g (0.035 mol) of 2'-nitro-3'-chloroacetophenone, in solution in 50 ml of acetic acid, are treated with 1.81 ml (0.0354 mol) of bromine at room temperature. After stirring for 12 hours, evaporation of the acetic acid leads to a yellow precipitate being obtained: 2'-nitro-3'-chloro-2-bromoacetophenone:

Yield 85%.

1.5 g (0.0061 mol) of 2'-nitro-3'-chloro-2-(methylthio) acetophenone are prepared by addition at 0° C. of 1.3 g (0.018 mol) of sodium methanethiolate in solution in 10 ml of methanol to 4.7 g (0.0168 mol) of 2'-nitro-3'-chloro-2-bromoacetophenone obtained above.

1.5. g (0.0061 mol) of 2'-nitro-3'-chloro-2-(methylthio) acetophenone are dissolved in 1.6 ml (0.012 mol) of N,N-dimethylformamide dimethyl acetal according to the procedure described in Example No. 1 and are heated at 70° C. and then, after isolation of the intermediate enaminone, are treated with 2 ml (0.042 mol) of hydrazine hydrate according to the procedure described in Example No. 1. After purification by passing through a silica column (heptane/ethyl acetate 75/25), 600 mg of the desired compound are obtained:

Yield 36%. M.p=169° C.

EXAMPLE 21

3-(3-Bromophenyl)-4-(methylsulfonyl)pyrazole (compound 147)

27.8 g (0.1 mol) of 3'-bromoacetophenone in solution in 300 ml of acetonitrile are treated with 10.2 g (0.1 mol) of sodium methylsulphinate and maintained at reflux for 8 hours. After cooling and evaporating the acetonitrile, the reaction mixture is washed with water and extracted with $CH_2Cl_2$. The crude residue obtained is purified by trituration in diisopropyl ether and leads to a yellow powder being obtained: (3'-bromo)(methylsulphonyl)acetophenone:

Yield 87%. M.p.=104° C.

1.1 g (0.004 mol) of (3'-bromo)(methylsulphonyl) acetophenone is dissolved in 20 ml (0.14 mol) of N,N-dimethylformamide dimethyl acetal and heated to 70° C. and then, after isolation of the intermediate enaminone, treated with 0.3 ml (0.006 mol) of hydrazine hydrate according to the procedure described in Example 1. After purification by trituration in diisopropyl ether, a beige powder is obtained:

Yield 44%. M.p.=140° C.

EXAMPLE 22

3-(2,2-Difluoro-1,3-benzodioxol-4-yl)-4-thiocyanatopyrazole (compound 148)

2.3 ml (0.048 mol) of hydrazine hydrate are added to a toluene solution (80 ml) containing 9.03 g (0.04 mol) of 3-oxo-3-(2,2-dichloro-1,3-benzodioxol-4-yl)propanonitrile, prepared according to Example No. 6, and 3.8 g (0.02 mol) of para-toluenesulphonic acid. The reaction mixture is heated at 80° C. for 2 hours. After cooling to room temperature, the reaction mixture is diluted with ethyl acetate, washed with water and with a saturated sodium chloride solution. After drying over $MgSO_4$, evaporation of the organic phase leads to a white powder being obtained which is purified by trituration in ether: 5-amino-3-(2,2-difluoro-1,3-benzodioxol-4-yl)pyrazole.

Yield 62%. M.p.=152° C.

0.45 ml (0.0088 mol) of bromine in methanolic solution (5 ml), cooled beforehand to −70° C., is added to a solution of 1.63 g (0.0168 mol) of potassium thiocyanate in 15 ml of methanol, cooled to −70° C. 1.92 g (0.008 mol) of 5-amino-3-(2,2-difluoro-1,3-benzodioxol-4yl)pyrazole in solution in 5 ml of methanol, cooled to −70° C., is then added while maintaining the temperature of the reaction mixture at −70° C. Stirring is maintained for 1 h 30 at −70° C. and then for approximately 30 minutes at room temperature. Treatment of the reaction mixture is carried out by addition of ethyl acetate, washing with water and with a saturated sodium chloride solution. After drying over $MgSO_4$, evaporation of the organic phase leads to the following being obtained: 5-amino-3-(2,2-difluoro-1,3-benzodioxol-4-yl)-4-thilocyanatopyrazole.

Yield 80%. M.p.=264° C.

0.94 ml (0.008 mol) of tert-butyl nitrite in solution in 5 ml of THF is added to a solution of 1.95 g (0.0065 mol) of 5-amino-4-thiocyanato-3-(2,2-difluoro-1,3-benzodioxol-4-yl)pyrazole in 25 ml of THF at 0° C. The reaction mixture is stirred for 1 h 30 at room temperature, then diluted with ethyl acetate and washed with water. After drying over $MgSO_4$ and evaporating the solvent, the residue obtained is chromatographed on a silica column and leads to 3-(2,2-difluoro-1,3-benzodioxol-4-yl)-1-(N-tetrahydrofuryl)-4-thiocyanatopyrazole being obtained.

Yield 20% (oil). Analysis No. 44694.

0.33 g (0.00094 mol) of the aminal obtained above is deprotected by being dissolved at room temperature in 10 ml of methanol treated with 0.033 g (0.00018 mol) of para-toluenesulphonic acid. After stirring for 1 hour at room temperature, the reaction mixture is diluted with ethyl acetate and washed with a saturated sodium bicarbonate solution. Drying over $MgSO_4$ and evaporation of the organic phase leads to a pale yellow powder being obtained: 3-(2,2-difluoro-1,3-benzodioxol-4-yl)-4-thiocyanatopyrazole:

Yield 98%. M.p.=163° C.

EXAMPLE 23

1-Methyl-3-(2,3-dichlorophenyl)-4-chloropyrazole (compound 149)

1.5 g of 4-chloro-3-(2,3-dichlorophenyl) pyrazole and 0.40 g of dimethyl methylphosphonate are heated at 150° C. for 1 hour. After returning to room temperature, the mixture is taken up in a saturated aqueous $NaHCO_3$ solution and extracted with 2×50 ml of $CH_2Cl_2$. The combined organic phases are dried over $Na_2SO_4$ and concentrated under reduced pressure. The crude solid is purified by liquid chromatography on a silica column (eluent: heptane/ethyl acetate [80/20]).

EXAMPLE 24

The following 4-chloro-3(5)-(substituted)phenyl-1-R-pyrazoles of formulae I or Ia are prepared as in Example 23:

| COMPOUND No. | Y | Z | R | I (%) | Ia (%) | M.p. (°C.) or analysis |
|---|---|---|---|---|---|---|
| 150 | $OCF_2$ | O | $CH_3$ | 100 | | 60 |
| 151 | $OCF_2$ | O | $CH_3$ | | 100 | oil |
| 152 | Cl | Cl | $CH_3$ | | 100 | 110 |
| 153 | Cl | Cl | $CH_3$ | 100 | | oil |
| 154 | Cl | H | $CH_3$ | | 100 | 66 |

EXAMPLE 25

1-Benzyl-3-(5)-(2,2-difluoro-1,3-dioxolano)phenyl-4-chloropyrazole (compound 155)

1.00 g of 4-chloro-3-(2,2-difluoro-1,3-dioxolano) phenylpyrazole and 0.75 g of benzyl bromide in 20 ml of absolute methanol are added to a solution of sodium methoxide prepared from 0.10 g of pieces of sodium and 10 ml of absolute methanol at room temperature. The reaction mixture is stirred for 12 hours at room temperature, concentrated to dryness under reduced pressure and taken up in 80 ml of a water/ethyl acetate (1/1) mixture. The organic phase is dried over $MgSO_4$ and concentrated under reduced pressure. The crude solid is purified by liquid chromatography on a silica column (eluent: heptane/ethyl acetate [80/20]).

| COMPOUND No. | Y | Z | R | I (%) | Ia (%) | M.p. (°C.) or analysis |
|---|---|---|---|---|---|---|
| 156 | $OCF_2$ | O | $CH_2C_6H_5$ | 70 | 30 | oil |
| 157 | $OCF_2$ | O | $SO_2N(CH_3)_2$ | 100 | | 50 |

EXAMPLE 26

1-(2-Cyanoethyl)-4-chloro-3-(2,2-difluoro-3-dioxolano)phenylpyrazole (compound 158)

1.00 g of 4-chloro-3-(2,2-difluoro-1,3-dioxolano) phenylpyrazole and 0.20 g of acrylonitrile are dissolved in 2.0 ml of dioxane. 0.02 ml of a 40% solution of Triton B in methanol is added. The reaction mixture is stirred for 12 hours at room temperature and concentrated to dryness under reduced pressure. The residual solid is triturated with 10 ml of heptane, recovered by filtration and dried under reduced pressure.

M.p.: 83° C.

EXAMPLE 27

1-[(Trimethylsilyl)methyl]-4-chloro-3-(2-nitro-3-chlorophenyl)pyrazole (compound 159)

0.85 g of anhydrous potassium carbonate is added to a solution of 1.30 g of 4-chloro-3-(2-nitro-3-chlorophenyl) pyrazole and 0.70 g of (trimethylsilyl)methyl chloride in 30 ml of N,N-dimethylformamide. The reaction mixture is stirred for 12 hours at room temperature and diluted with 100 ml of an ether/$H_2O$ (1/1) mixture. The ether phase is dried over $MgSO_4$ and concentrated under reduced pressure. The residual oil is purified by liquid chromatography on a Silica column (eluent: heptane/ethyl acetate [50/50]).

EXAMPLE 28

The following compounds are prepared as in Example 27:

| COMPOUND No. | Y | Z | R | I (%) | Ia (%) | M.p. (°C.) or analysis |
|---|---|---|---|---|---|---|
| 160 | $NO_2$ | Cl | $CH_2S$—($pClC_6H_4$) | 80 | 20 | 88 |
| 161 | $NO_2$ | Cl | $CH_2SCH_3$ | 80 | 20 | 65 |
| 162 | $NO_2$ | Cl | $CH_2OCH_3$ | 100 | | 124 |
| 163 | $NO_2$ | Cl | $CH_2OCH_3$ | | 100 | 128 |
| 164 | $NO_2$ | Cl | $CH_2O(CH_2)_2OCH_3$ | 100 | | 57 |
| 165 | $NO_2$ | Cl | $CH_2O(CH_2)_2Si(CH_3)_3$ | 53 | 47 | oil |
| 166 | $NO_2$ | Cl | $CH_2SCN$ | 84 | 16 | 99 |
| 167 | $NO_2$ | Cl | $CH_2SO_2CH_3$ | 50 | 50 | 62 |
| 168 | $NO_2$ | Cl | $CH_2(o-NO_2C_6H_4)$ | | 100 | 115 |
| 169 | $NO_2$ | Cl | $CH_2CO(4-CH_3OC_6H_4)$ | 100 | | 146 |
| 170 | $NO_2$ | Cl | $CH_2OCH_2C_6H_5$ | 80 | 20 | 84 |
| 171 | H | Cl | $CH_2CH_2Cl$ | 80 | 20 | oil |

EXAMPLE 29

1-(Chlorothioformyl)-4-chloro-(2,2-difluoro-1,3-dioxolano)phenylpyrazole (compound 172)

1.00 g of 4-chloro-3-(2,2-difluoro-1,3-dioxolano) phenylpyrazole and 0.15 ml of thiophosgene in solution in 50 ml of toluene are heated, at reflux of the thiophosgene (70° C.), for 2 hours. The reaction mixture is concentrated to dryness under reduced pressure. The residue is purified by liquid chromatography on a silica column (heptane/AcOEt. [90/10]).

M.p.: 85° C.,

EXAMPLE 30

1-Benzoyl-4-chloro-3-(2,2-difluoro-3-dioxolano) phenylpyrazole (compound 173)

0.55 g of benzoyl chloride diluted in 10 ml of anhydrous THF are added dropwise to a solution, cooled to +10° C., of 1.0 g of 4-chloro-3-(2,2-difluoro-1,3-dioxolano) phenylpyrazole, 0.08 g of DMAP and 0.55 ml of triethylamine in 20 ml of anhydrous THF. Stirring is continued for 2 hours at room temperature. The reaction mixture is concentrated to dryness under reduced pressure and taken up in 80 ml of an $H_2O$-ethyl acetate (1/1) mixture. The organic phase is dried over $MgSO_4$ and concentrated under reduced pressure.

M.p.: 85° C.

EXAMPLE 31

The following compounds are prepared as in Example 30:

| COMPOUND No. | Y | Z | R | M.p. (°C.) or analysis |
|---|---|---|---|---|
| 174 | $OCF_2$ | O | $COCH_3$ | 125 |
| 175 | $CH_3$ | Cl | $COCH_3$ | 63 |
| 176 | $NO_2$ | Cl | $COCH_3$ | 158 |

EXAMPLE 32

1-(Methoxycarbonyl)-4-chloro-3-(2,2-difluoro-1,3-dioxolano)phenylpyrazole (compound 177)

5 ml of methyl chloroformate, diluted in 10 of anhydrous THF, are added dropwise to a solution, cooled to 0° C., of 1.0 g of 4-chloro-3-(2,2-difluoro-1,3-dioxolano) phenylpyrazole, 0.08 g of DMAP and 0.55 mg of triethylamine in 20 ml of anhydrous THF. Stirring is continued for 2 h at room temperature. The reaction mixture is concentrated to dryness under reduced pressure and taken up in 80 ml of a $H_2O$—AcOEt (1/1) mixture. The organic phase is dried over $MgSO_4$ and concentrated under reduced pressure.

Melting point: 75° C.

By carrying out the preparation as above, 1-benzyloxycarbonyl-4chloro-3-(2,2-difluoro-1,3-dioxolano)phenylpyrazole (compound 178) is obtained.

Melting point: 83° C.

EXAMPLE 33

1-(tert-Butyloxycarbonyl)-4-chloro-3-(2,2-difluoro-1,3-dioxolano)phenylpyrazole (compound 179)

1.00 g of anhydrous di(tert-butyloxy)carbonyl, diluted in 10 g of acetonitrile, is added dropwise to a solution of 1.0 g of 4-chloro-3-(2,2-difluoro-1,3-dioxolano)phenylpyrazole, 0.045 g of DMAP 0.55 ml of triethylamine in 20 ml acetonitrile. Stirring is continued for 2 hours at room temperature. The reaction mixture is concentrated to dryness under reduced pressure. The residual solid is purified by livid chromatography on a silica column (eluent: heptane/ ethyl acetate [80/20]). The solid has the consistency of a foam.

EXAMPLE 34

1-(Phenoxycarbonyl-4-chloro-3-(2-nitro-3-chlorophenyl)pyrazole of (compound 180)

1.0 ml of phenyl chloroformate is added, in small portions, to a solution, cooled to 0° C., of 1.3 g of 4-chloro-3-(2-nitro-3-chlorophenyl)pyrazole in 20 ml of pyridine. Stirring is continued for 8 hours at room temperature. The reaction mixture is concentrated dryness under reduced pressure and taken up in 100 ml of an $H_2O$/ethyl acetate (1/1) mixture. The organic phase is dried over $MgSO_4$ and concentrated under reduced pressure. The residual solid is purified by recrystallisation from diisopropyl ether.

Melting point: 123° C.

EXAMPLE 35

The following compounds are prepared as in Example 34:

| Compound No. | Y | Z | R | M.p. (°C.) or analysis |
|---|---|---|---|---|
| 181 | $NO_2$ | Cl | $C(O)S\ C_2H_5$ | 109 |
| 182 | $NO_2$ | Cl | $CO_2C(CH_3)_2CO_2C_2H_5$ | 219 |
| 183 | $NO_2$ | Cl | $CO_2CHCH_2$ | 118 |
| 184 | $NO_2$ | Cl | $CO_2(p-NO_2C_6H_4)$ | 185 |
| 185 | $NO_2$ | Cl | $CO_2CH_2CHCl_2$ | 130 |

EXAMPLE 36

1-Isopropylaminocarbonyl-4-chloro-3-(2,2-difluoro-1,3-dioxolano)phenylpyrazole (compound 186)

0.45 g of isopropyl isocyanate is added dropwise to a solution of 1.0 g of 4-chloro-3-(2,2-difluoro-1,3-dioxolano) phenylpyrazole and 0.50 g of triethylamine in 20 ml of anhydrous DMF. Stirring is continued for 2 hours at room temperature. The treatment is identical to that of Example 32.

Melting point: 135° C.

EXAMPLE 37

1-(4-Methylphenylsulphonyl)-4-chloro-3-(2,2-difluoro-1,3-dioxolano)phenylpyrazole (compound 187)

0.75 g of tosyl chloride is added, in small portions, to a solution of 1.0 g of 4-chloro-3-(2,2-difluoro-1,3-dioxolano) phenylpyrazole and 0.5 ml of pyridine in 20 ml of toluene. Stirring is continued for 2 hours at 40° C. The treatment is identical to that of Example 32. The residual solid is purified by liquid chromatography on a silica column (eluent: heptane/ethyl acetate [80/20]).

Melting point: 100° C.

EXAMPLE 38

In Vivo Test on *Botrytis Cinerea* on Excised Tomato Leaf (Strains Sensitive and Resistant to Benzimidazoles)

An aqueous suspension of the active material to be tested is prepared, by fine milling, having the following composition:

active materials: 60 mg surface-active agent Tween 80 (oleate of polyoxyethylenated derivative of sorbitan) diluted to 10% in water: 0.3 ml made up to 60 ml with water.

This aqueous suspension is then diluted with water to obtain the desired concentration of active material.

Tomatoes cultivated under glass (variety Marmande), 30 days old, are treated by spraying with aqueous suspensions as defined above and at various concentrations of the test compound.

After 24 hours, the leaves cut and put in a Petri dish (diameter 14 cm), the bottom of which was covered beforehand with a wet filter paper disc (10 leaflets per dish).

The inoculum is then introduced, using a syringe, by deposition of drops (3 per leaflet) of a suspension of spores of *Botrytis cinerea*, which are sensitive to benzimidazoles or resistant to benzimidazoles, obtained from 15-day cultures and then suspended at a concentration of 150,000 units per $cm^3$.

Inspection is carried out 6 days after infection by comparison with an untreated control.

Under these conditions, at a dose of 1 g/l, a good (at least 75%) or total protection is observed with the following compounds:

Botrytis sensitive to benzimidazoles: 9, 13, 17, 19, 21, 22, 23, 24, 25, 71, 73, 74, 88, 95, 99, 100, 104, 105, 107, 108, 113, 114, 116, 120, 122, 123, 124, 128, 133, 135, 147, 166, 172, 173, 175, 176, 177, 179, 180, 181, 182, 183, 184, 185.

EXAMPLE 39

In Vivo Test on *Piricularia Oryzae* Responsible for Piriculariosis in Rice

An aqueous suspension of the active material to be tested is prepared, having the following composition:

active material: 60 mg surface-active agent TWeen 80 (oleate of polyoxyethylenated derivative of sorbitan) diluted to 10% in water: 0.3 ml made up to 60 ml with water.

This aqueous suspension is then diluted with water to obtain the desired concentration of active material.

Rice, seeded in small pots in a 50/50 mixture of enriched peat and pozzolana, is treated at the 10 cm high stage by spraying with the above aqueous suspension.

After 24 hours, an aqueous suspension of spores of *Piricularia oryzae*, obtained from a 15-day culture and then suspended at a concentration of 100,000 units per $cm^3$, is applied to the leaves.

The rice plants are incubated for 24 hours (25° C., 100% relative humidity) and are then put in an observation cell, under the same conditions, for 7 days.

Reading is carried out 6 days after infection.

Under these conditions, at a dose of 1 g/l, a good (at least 75%) or total protection is observed with the following compounds:

12, 17, 19, 21, 24, 25, 72, 78, 81, 84, 87, 95, 99, 100, 101, 103, 104, 105, 107, 108, 110, 111, 112, 113, 114, 116, 117, 118, 120, 122, 123, 124, 127, 128, 129, 130, 133, 134, 135, 141, 166, 172, 173, 174, 175, 176, 177, 179, 180, 181, 182, 183, 184, 185.

EXAMPLE 40

In vivo Test on *Plasmopara Viticola*

An aqueous suspension of the active material to be tested is prepared, by fine milling, having the following composition:

active material: 60 mg surface-active agent Tween 80 (oleate of polyoxyethylenated derivative of sorbitan) diluted to 10% in water: 0.3 ml made up to 60 ml with water.

This aqueous suspension is then diluted with water to obtain the desired concentration of active material.

Vine cuttings (*Vitis vinifera*, variety Chardonnay) are cultivated in small pots. When these plants are 2 months old (8 to 10 leaf stage, 10 to 15 cm in height), they are treated by spraying with the above aqueous suspension.

Plants used as controls are treated with an aqueous solution which does not contain the active material.

After drying for 24 hours, each plant is infected by spraying with an aqueous suspension of spores-of *Plasmopara viticola*, obtained from a 17-day culture and then suspended at a concentration of 100,000 units per $cm^3$.

The infected plants are then incubated for two days at approximately 18° C., in an atmosphere saturated with moisture and then for 5 days at approximately 20°–22° C. at 90–100% relative humidity.

Reading is carried out 7 days after infection, by comparison with the control plants.

Under these conditions, at a dose of 1 g/l, a good (at least 75%) or total protection is observed with the following compounds: 13, 19, 20, 21, 22, 24, 25, 64, 74, 77, 80, 81, 82, 102, 104, 106, 107, 109, 111, 113, 125, 127, 131, 133, 134, 139, 142, 144, 186.

These results clearly show the good fungicidal properties of the derivatives according to the invention against fungal diseases of plants due to fungi belonging to the most diverse families, such as the Phycometes, Basidiomycetes, Ascomycetes, Adelomycetes or Fungi Imperfecti, in particular the Botrytis species, *Piricularia oryzae*, Alternaria and grape downy mildew.

In fact, the compounds according to the invention are rarely used alone for the practical use. These compounds are most often part of compositions. These compositions, which can be used as herbicidal agents, contain a compound according to the invention, as described earlier, as active material mixed with solid or liquid vehicles, which are acceptable in agriculture, and surface-active agents which are also acceptable in agriculture. In particular, the inert and conventional vehicles and the conventional surface-active agents can be used. These compositions also form part of the invention.

These compositions can also contain any kind of other ingredients such as, for example, protective colloids, adhesives, thickening agents, thixotropic agents, penetrating agents, stabilising agents, sequestering agents and the like. More generally, the compounds used in the invention can be combined with all the solid or liquid additives corresponding to the conventional formulating techniques.

Generally, the compositions according to the invention usually contain from approximately 0.05 to 95% (by weight) of a compound according to the invention, one or more solid or liquid vehicles and, optionally, one or more surface-active agents.

In the present account, the term "vehicle" denotes a natural or synthetic, organic or inorganic material with which the compound is combined facilitate its application to the plant, to seeds or to the ground. This vehicle is thus generally inert and it must be acceptable in agriculture, especially on the treated plant. The vehicle can be solid (clays, natural or synthetic silicates, silica, resins, waxes, solid fertilisers and the like) or liquid (water, alcohols, especially butanol, and the like).

The surface-active agent can be an emulsifying, dispersing or wetting agent of ionic or nonionic type or a mixture of such surface-active agents. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols, especially alkylphenols or arylphenols), salts of esters of sulphosuccinic acids, taurine derivatives (especially alkyltaurates), phosphoric esters of polyoxyethylenated phenols or alcohols, esters of fatty acids and polyols, and the derivatives of the above compounds containing sulphate, sulphonate and phosphate functional groups. The presence of at least one surface-active agent is generally indispensable when the compound and/or the inert vehicle is not soluble in water and the carrier agent for application is water.

The compositions for agricultural use according to the invention can thus contain the active materials according to the invention within very wide limits, ranging from 0.05% to 95% (by weight). Their surface-active agent content is advantageously of between 5% and 40% by weight.

These compositions according to the invention are themselves in fairly diverse, solid or liquid forms.

There may be mentioned, as forms of solid compositions, the powders for dusting (with a content of compound which can range up to 100%) and the granules, especially those obtained by extrusion, by compacting, by impregnation of a granulated support, or by granulation from a powder (the content of compound in these granules being between 0.5 and 80% for the latter cases).

The compounds of formula (I) can also be used in the form of powders for dusting; it is also possible to use a composition comprising 50 g of active material and 950 g of talc; it is also possible to use a composition comprising 20 g of active material, 10 g of finely divided silica and 970 g of talc; these constituents are mixed and milled and the mixture is applied by dusting.

There may be mentioned, as forms of liquid compositions or those intended to constitute liquid compositions at the time of application, solutions, in particular water-soluble concentrates, emulsifiable concentrates, emulsions, suspension concentrates, aerosols, wettable powders (or powder to be sprayed), or pastes.

The emulsifiable or soluble concentrates most often comprise 10 to 80% of active material while emulsions or solutions ready for application contain 0.001 to 20% of active material.

In addition to the solvent, the emulsifiable concentrates can contain, when this is necessary, 2 to 20% of suitable additives such as stabilising agents, surface-active agents, penetrating agents, corrosion inhibitors, dyes or the above-mentioned adhesives.

From these concentrates, it is possible to obtain, by dilution with water, emulsions of any desired concentration, which are particularly suitable for application to crops.

The compositions of some emulsifiable concentrates are given here as examples:

EC Example 1:

| active material | 400 g/l |
| alkali metal dodecylbenzenesulphonate | 24 g/l |
| oxyethylenated nonylphenol, containing 10 molecules of ethylene oxide | 16 g/l |
| cyclohexanone | 200 g/l |
| aromatic solvent | qs 1 liter |

Another emulsifiable concentrate formula uses:
EC Example 2:

| active material | 250 g |
| epoxidised vegetable oil | 25 g |
| mixture of alkylaryl sulphonate and ether of polyglycol and fatty alcohols | 100 g |
| dimethylformamide | 50 g |
| xylene | 575 g |

The suspension concentrates, also applicable in spraying, are prepared so as to obtain a stable fluid product which does not settle out and they generally contain from 10 to 75% of active material, from 0.5 to 15% of surface-active agents, from 0.1 to 10% of thixotropic agents and from 0 to 10% of suitable additives, such as antifoaming agents, corrosion inhibitors, stabilising agents, penetrating agents and adhesives and, as vehicle, water or an organic liquid in which the active material is insoluble or nearly insoluble: certain organic solid materials or inorganic salts can be dissolved in the vehicle to aid in preventing sedimentation or as antigels for water.

A suspension concentrate composition is given here as an example:
SC Example 1:

| compound | 500 g |
| polyethoxylated tristyrylphenyl phosphate | 50 g |
| polyethoxylated alkylphenol | 50 g |
| sodium polycarboxylate | 20 g |
| ethylene glycol | 50 g |
| organopolysiloxane oil (antifoaming agent) | 1 g |
| polysaccharide | 1.5 g |
| water | 316.5 g |

Wettable powders (or powder to be sprayed) are generally prepared so that they contain 20 to 95% of active material, and they generally contain, in addition to the solid vehicle, from 0 to 30% of a wetting agent from 3 to 20% of a dispersing agent and, when this is necessary, from 0.1 to 10% of one or more stabilising agents and/or other additives, such as penetrating agents, adhesives, or anticlumping agents, dyes, and the like.

To obtain powders to be sprayed or wettable powders, the active materials are intimately mixed, in suitable mixers, with the additional substances and the mixture is milled with mills or other suitable grinders. Powders to be sprayed are thereby obtained with advantageous wettability and suspensibility; they can be suspended in water at any desired concentration and these suspensions can be used very advantageously in particular for application to plant leaves.

Pastes can be produced in place of wettable powders. The conditions and modes of production and use of these pastes are similar to those of wettable powders or powders to be sprayed.

Various wettable powder (or powder to be sprayed) compositions are given here as examples:

WP Example 1:

| active material (compound No. 1) | 50% |
|---|---|
| ethoxylated fatty alcohol (wetting agent) | 2.5% |
| ethoxylated phenylethylphenol (dispersing agent) | 5% |
| chalk (inert vehicle) | 42.5% |

WP Example 2:

| active material (compound No. 1) | 10% |
|---|---|
| C13 branched-type synthetic oxo alcohol, ethoxylated with 8 to 10 molecules of ethylene oxide (wetting agent) | 0.75% |
| neutral calcium lignosulphonate (dispersing agent) | 12% |
| calcium carbonate (inert vehicle) | qs 100% |

WP Example 3:

This wettable powder contains the same ingredients as in the above example, in the proportions below:

| active material | 75% |
|---|---|
| wetting agent | 1.50% |
| dispersing agent | 8% |
| calcium carbonate (inert vehicle) | qs 100% |

WP Example 4:

| active material (compound No. 1) | 90% |
|---|---|
| ethoxylated fatty alcohol (wetting agent) | 4% |
| ethoxylated phenylethylphenol (dispersing agent) | 6% |

WP Example 5:

| active material (compound No. 1) | 50% |
|---|---|
| mixture of anionic and nonionic surface-active agents (wetting agent) | 2.5% |
| sodium lignosulphonate (dispersing agent) | 5% |
| kaolin clay (inert vehicle) | 42.5% |

Aqueous dispersions and emulsions, for example the compositions obtained by diluting a wettable powder or an emulsifiable concentrate according to the invention with water, are within the general scope of the present invention.

Emulsions can be of the water-in-oil or oil-in-water type and they can have a thick consistency, like that of a "mayonnaise".

The compounds according to the invention can be formulated in the form of water-dispersable granules, also within the scope of the invention.

These dispersible granules, with a bulk density generally of between approximately 0.3 and 0.6, have a particle size generally of between approximately 150 and 2000 and preferably between 300 and 1500 microns.

The active material content of these granules is generally between approximately 1% and 90%, and preferably between 25% and 90%.

The rest of the granule is essentially composed of a solid vehicle and, optionally, of surface-active adjuvants which confer water-dispersibility properties on the granule. These granules can be essentially of two distinct types according to whether the vehicle held is soluble or insoluble in water. When the vehicle is water-soluble, it can be inorganic or, preferably, organic. Excellent results were obtained with urea. In the case of an insoluble vehicle, the latter is preferably inorganic, such as, for example, kaolin or bentonite. It is then advantageously accompanied by surface-active agents (in a proportion of 2 to 20% by weight of the granule) of which more than half consists of, for example, at least one dispersing agent essentially anionic, such as an alkali metal or alkaline-earth metal polynaphthalenesulphonate or an alkali metal or alkaline-earth metal lignosulphonate; the remainder consisting of nonionic or anionic wetting agents such as an alkali metal or alkaline-earth metal alkylnaphthalenesulphonate.

Moreover, although this is not indispensible, it is possible to add other adjuvants such as antifoaming agents.

The granules according to the invention can be prepared by mixing the necessary ingredients and then granulating according to several techniques known per se (granulator, fluid bed, sprayer, extrusion, and the like). The preparation generally finishes with a grinding followed by a sieving to the particle size chosen within the limits mentioned above.

They are preferably obtained by extrusion, by carrying out the preparation as indicated in the examples below.

F Example 6: Dispersible Granules

90% by weight of active material (compound No. 1) and 10% of urea in the form of pearls are mixed in a mixer. The mixture is then milled in a pin mill. A powder is obtained which is moistened with approximately 8% by weight of water. The moist powder is extruded in a perforated-roller extruder. A granular material is obtained which is dried, and then crushed and sieved, so as to respectively keep only the granules with a size of between 150 and 2000 microns.

F Example 7: Dispersible Granules

The following constituents are mixed in a mixer:

| active material (compound No. 1) | 75% |
|---|---|
| wetting agent (sodium alkylnaphthalene-sulphonate | 2% |
| dispersing agent (sodium polynaphthalene-sulphonate) | 8% |
| water-insoluble inert vehicle (kaolin) | 15% |

This mixture is granulated on a fluid bed in the presence of water and then dried, crushed and sieved so as to obtain granules with a size of between 0.15 and 0.80 mm.

These granules can be used alone or in solution or dispersion in water so as to obtain the required dose. They can also be used to prepare combinations with other active materials, especially fungicides, the latter being in the form of wettable powders or granules or aqueous suspensions.

As regards the compositions which are suitable for storage and transportation, they most advantageously contain from 0.5 to 95% (by weight) of active substance.

Another subject of the invention is the use of the compounds according to the invention for combating fungal diseases in plants by preventative or curative treatment of the latter or of their growth site.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

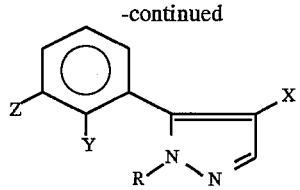

Ia wherein:
X is:
- a hydrogen or halogen atom,
- a nitro, cyano or thiocyanato group,
- a $C_1$–$C_4$ alkyl, $C_2$–$C_4$ alkenyl, $C_2$–$C_4$ alkynyl, $C_1$–$C_4$ alkoxy or $C_1$–$C_4$ alkylthio group, each of said groups being optionally halogenated,

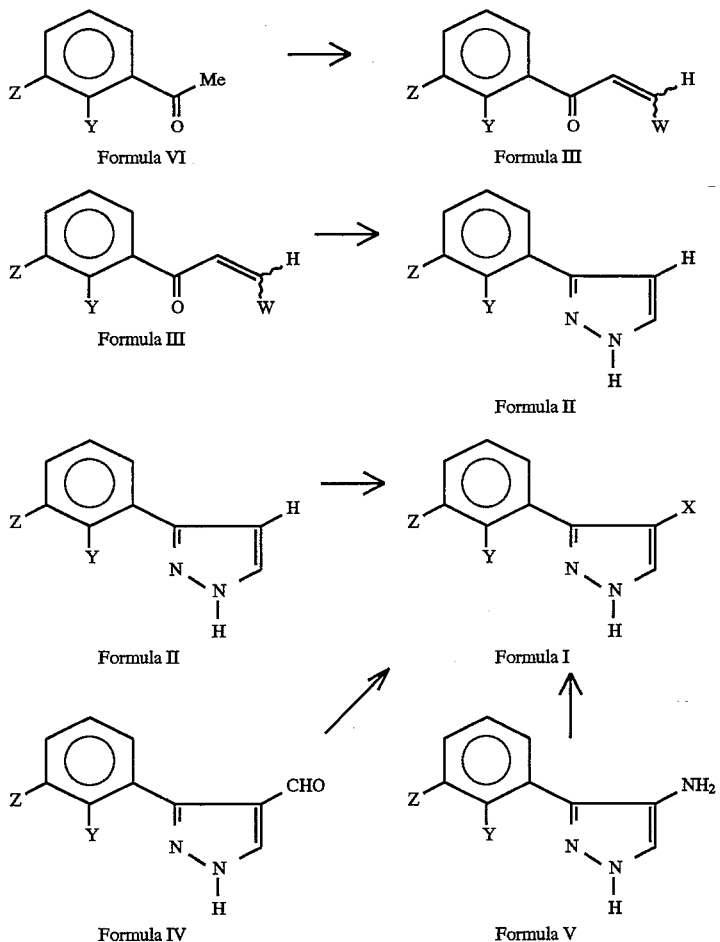

What is claimed:
1. A compound of the formula

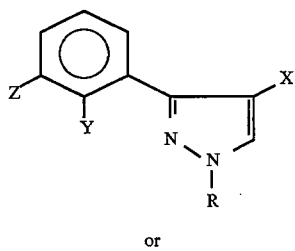

I or phenyl or phenoxy, each of which is optionally substituted by $C_1$–$C_3$ alkyl, $C_1$–$C_3$ haloalkyl or $C_1$–$C_3$ alkoxy, an amino group, optionally bearing one or two substituents selected from the group consisting of $C_1$–$C_4$ alkyl and phenyl, a ($C_1$–$C_4$ alkyl)carbonyl, carbamoyl, carboxyl or benzoyl group, a $C_1$–$C_4$ alkylsulphinyl or $C_1$–$C_4$ alkylsulphonyl group;
each of Y and Z, which are identical or different, is:
- a hydrogen atom, provided that Y and Z cannot both be hydrogen,
- a halogen atom,
- a hydroxyl, nitro, nitroso, cyano or thiocyanato group, an amino group, optionally bearing one or two substituents selected from the group consisting of $C_1$–$C_4$ alkyl and phenyl, $C_1$–$C_4$ alkyl, $C_1$–$C_4$ alkoxy, $C_1$–$C_4$ alkylthio, $C_1$–$C_4$ hydroxyalkyl, $C_2$–$C_4$ alkenyl, $C_2$–$C_4$ alkynyl, $C_1$–$C_4$ alkylsulphinyl or $C_1$–$C_4$ alkylsulphonyl group, each of said groups being optionally halogenated, phenyl, phenyloxy, phenylthio or benzyl, each of which is optionally substituted on the nucleus by $C_1$–$C_3$ alkyl, $C_1$–$C_3$ haloalkyl or $C_1$–$C_3$ alkoxy, a formyl, acetyl, ($C_1$–$C_4$ alkyl)thiocarbonyl, ($C_1$–$C_4$ alkoxy)thiocarbonyl, mono- or di($C_1$–$C_4$ alkyl)aminocarbonyl, mono- or di($C_1$–$C_4$ alkyl)aminothiocarbonyl, carboxyl, carboxylate or carbamoyl group, the alkyl portion of said groups being optionally substituted by at least one halogen atom, or benzoyl, optionally substituted on the nucleus by $C_1$–$C_3$ alkyl, $C_1$–$C_3$ haloalkyl or $C_1$–$C_3$ alkoxy;

R is:
a) a hydrogen atom, a nitro, amino, hydroxyl, cyano, $C_1$–$C_6$ alkyl or $C_1$–$C_6$ haloalkyl group;
b) a group $S(O)_m$—$R_1$, wherein:
  m is an integer equal to zero or two, and
  $R_1$ is:
    either, when m is equal to zero:
      a $C_1$–$C_6$ haloalkyl group,
      a phenyl or 3-pyridyl group, each of which is optionally substituted by at least one halogen atom or one nitro, $C_1$–$C_4$ alkyl, $C_1$–$C_4$ haloalkyl, $C_1$–$C_4$ alkoxy or $C_1$–$C_4$ haloalkoxy group;
    or, when m is equal to two:
      a $C_1$–$C_6$ alkyl or $C_1$–$C_6$ alkoxy group, each of which is optionally substituted by one or more halogen atoms or $C_1$–$C_3$ alkoxy groups;
      a $C_3$–$C_6$ cycloalkyl group;
      a $C_3$–$C_6$ alkenyl, $C_3$–$C_6$ alkynyl or $C_3$–$C_6$ alkenoxy group;
      a phenyl group, optionally substituted by 1 to 5 substituents selected from the group consisting of halogen, nitro, $C_1$–$C_4$ alkyl, $C_1$–$C_4$ haloalkyl, $C_1$–$C_4$ alkoxy and $C_1$–$C_4$ haloalkoxy;
c) a group $CH_2$—$NR_2R_3$, wherein:
  $R_2$ is:
    $C_1$–$C_6$ alkyl, optionally bearing a substituent selected from the group consisting of cyano, $C_1$–$C_6$ alkoxy, $C_3$–$C_7$ cycloalkyl, ($C_1$–$C_6$ alkyl)carbonyl, ($C_1$–$C_6$ alkoxy)carbonyl, mono($C_1$–$C_6$ alkyl)aminocarbonyl, di($C_1$–$C_6$ alkyl)aminocarbonyl, $C_1$–$C_6$ alkylsulphinyl, $C_1$–$C_6$ alkylsulphonyl and di($C_1$–$C_6$ alkyl)amino;
    $C_2$–$C_6$ alkenyl or $C_2$–$C_6$ alkynyl;
    $C_3$–$C_7$ cycloalkyl;
    phenyl or benzyl, each of which optionally bears a substituent selected from the group consisting of halogen, cyano, $C_1$–$C_6$ alkyl, $C_1$–$C_6$ alkoxy, $C_1$–$C_6$ haloalkyl having 1 to 9 halogen atoms, $C_1$–$C_6$ haloalkoxy having 1 to 9 halogen atoms, ($C_1$–$C_6$ alkyl)carbonyl and ($C_1$–$C_6$ alkoxy)carbonyl;
  $R_3$ is:
    a group Het, Het-($C_1$–$C_6$ alkyl), Het-($C_3$–$C_6$ alkenyl) or Het-($C_3$–$C_6$ alkynyl), each of which optionally bears a substituent selected from the group consisting of halogen, cyano, $C_1$–$C_6$ alkyl, $C_1$–$C_6$ alkoxy, $C_1$–$C_6$ haloalkyl having 1 to 9 halogen atoms, $C_1$–$C_6$ haloalkoxy having 1 to 9 halogen atoms, ($C_1$–$C_6$ alkyl)carbonyl and ($C_1$–$C_6$ alkoxy)carbonyl, wherein Het is a heterocyclic radical having 5 to 7 atoms, of which 1 to 3 are heteroatoms selected from the group consisting of nitrogen, oxygen and sulphur, optionally bearing a substituent selected from the group consisting of halogen, cyano, $C_1$–$C_6$ alkyl, $C_1$–$C_6$ alkoxy, $C_1$–$C_6$ haloalkyl having 1 to 9 halogen atoms, $C_1$–$C_6$ haloalkoxy having 1 to 9 halogen atoms, ($C_1$–$C_6$ alkyl)carbonyl and ($C_1$–$C_6$ alkoxy)carbonyl;
    di($C_1$–$C_6$ alkyl)amino($C_1$–$C_6$ alkyl), $C_3$–$C_7$ cycloalkyl, ($C_3$–$C_7$ cycloalkyl)($C_1$–$C_4$ alkyl) or phenethyl, optionally bearing a substituent selected from the group consisting of halogen, cyano, $C_1$–$C_4$ alkyl and $C_1$–$C_4$ alkoxy;
  $R_2$ and $R_3$ can additionally form, with the nitrogen atom to which they are joined, a nitrogen-containing ring having 6 atoms, 4 of which are carbon atoms, optionally substituted, and the fifth of which is a carbon atom or a heteroatom selected from the group consisting of oxygen, sulphur and nitrogen which can be optionally substituted by $C_1$–$C_6$ alkyl, the nitrogen-containing ring itself optionally bearing one or two substituents selected from the group consisting of cyano, ($C_1$–$C_6$ alkyl)carbonyl, ($C_1$–$C_6$ alkoxy)carbonyl, mono($C_1$–$C_6$ alkyl)aminocarbonyl, di($C_1$–$C_6$ alkyl)aminocarbonyl, $C_1$–$C_6$ alkylsulphinyl, $C_1$–$C_6$ alkylsulphonyl, phenylsulphinyl and phenylsulphonyl;
d) a group $(CH_2)_m$—$R_4$, wherein:
  m is equal to 1 or 2,
  $R_4$ is cyano, nitro, ($C_1$–$C_4$ alkyl)carbonyl, phenylcarbonyl, ($C_1$–$C_4$ alkoxy)carbonyl, mono($C_1$–$C_4$ alkyl)aminocarbonyl, di($C_1$–$C_4$ alkyl)aminocarbonyl, $P(O)$ ($C_1$–$C_4$ alkoxy)$_2$, $P(O)$(benzyloxy)$_2$, $P(O)$(phenoxy)$_2$, tri($C_1$–$C_4$ alkyl)silyl or phenyl, wherein the alkyl portions of said groups are optionally halogenated and the phenyl nucleus of the aromatic radicals optionally bears 1 to 5 substituents selected from the group consisting of halogen, nitro, $C_1$–$C_4$ alkyl, $C_1$–$C_4$ alkoxy, $C_1$–$C_4$ haloalkyl, $C_1$–$C_4$ haloalkoxy and ($C_1$–$C_4$ alkoxy)carbonyl;
e) a group $CH(R_5)$—X—$R_6$, wherein:
  $R_5$ is hydrogen or $C_1$–$C_4$ alkyl,
  X is an oxygen atom or a group $S(O)_n$, wherein:
    n is an integer equal to zero or two,
  $R_6$ is:
    $C_1$–$C_4$ alkyl, optionally bearing a substituent selected from the group consisting of halogen, cyano, $C_1$–$C_4$ alkoxy, phenoxy, benzyloxy and tri($C_1$–$C_4$ alkyl)silyl, the phenyl nuclei being optionally substituted by 1 to 5 substituents selected from the group consisting of halogen, nitro, $C_1$–$C_4$ alkyl, $C_1$–$C_4$ alkoxy, $C_1$–$C_4$ haloalkyl and $C_1$–$C_4$ haloalkoxy;
    $C_3$–$C_6$ alkenyl or $C_3$–$C_6$ alkynyl;
    phenyl or benzyl, each of which optionally bears 1 to 5 substituents selected from the group consisting of halogen, nitro, $C_1$–$C_4$ alkyl, $C_1$–$C_4$ alkoxy, $C_1$–$C_4$ haloalkyl and $C_1$–$C_4$ haloalkoxy;
f) a group $CHR_7R_8$, wherein:
  $R_7$ is a hydrogen atom or a $C_1$–$C_4$ haloalkyl or $C_1$–$C_4$ alkoxy group, $R_8$ is a halogen atom or a hydroxyl, $C_1$–$C_6$ alkoxy or O—C(O)$R_9$ group wherein:
  $R_9$ is hydrogen, $C_1$–$C_6$ alkyl, $C_1$–$C_6$ haloalkyl, $C_2$–$C_4$ alkenyl, tetrahydrofuryl, tetrahydropyranyl or ($C_1$–$C_6$ alkoxy)carbonyl;

g) a group C(X)—$R_{10}$, wherein:
  X is an oxygen or sulphur atom,
  $R_{10}$ is:
    a hydrogen or halogen atom,
    a $C_1$–$C_6$ alkyl group, optionally bearing a substituent selected from the group consisting of halogen, cyano, nitro, ($C_1$–$C_4$ alkyl)carbonyl, ($C_1$–$C_4$ alkoxy)carbonyl, mono($C_1$–$C_4$ alkyl)aminocarbonyl, di($C_1$–$C_4$ alkyl)aminocarbonyl and $C_3$–$C_6$ cycloalkyl;
    a $C_3$–$C_6$ alkenyl or $C_3$–$C_6$ alkynyl group, optionally substituted by a phenyl which optionally bears 1 to 5 substituents selected from the group consisting of halogen, nitro, $C_1$–$C_4$ alkyl, $C_1$–$C_4$ alkoxy, $C_1$–$C_4$ haloalkyl and $C_1$–$C_4$ haloalkoxy;
    a phenyl, benzyl, 2-pyridyl, 3-pyridyl or 4-pyridyl group, the nuclei of each of which optionally bears 1 to 5 substituents selected from the group consisting of halogen, nitro, cyano, $C_1$–$C_4$ alkyl, $C_1$–$C_4$ alkoxy, $C_1$–$C_4$ haloalkyl, $C_1$–$C_4$ haloalkoxy, ($C_1$–$C_4$ alkyl)carbonyl and ($C_1$–$C_4$ alkoxy)carbonyl;
    a group CH($R_{11}$)—X—$R_{12}$, wherein:
      $R_{11}$ is a hydrogen atom or $C_1$–$C_4$ alkyl group,
      X is an oxygen atom or the group S(O)$_p$, wherein p is equal to zero or 2;
      $R_{12}$ is $C_1$–$C_4$ alkyl group, optionally substituted by a halogen atom or $C_1$–$C_4$ alkoxy group; a $C_3$–$C_6$ alkenyl or $C_3$–$C_6$ alkynyl group; a phenyl or benzyl group, optionally bearing 1 to 5 substituents selected from the group consisting of halogen, nitro, $C_1$–$C_4$ alkyl, $C_1$–$C_4$ alkoxy, $C_1$–$C_4$ haloalkyl and $C_1$–$C_4$ haloalkoxy;
    a group CH($R_{11}$)—N$R_{13}R_{14}$, wherein:
      $R_{11}$ is defined as above and
      each of $R_{13}$ and $R_{14}$, which are identical or different, is:
        $C_1$–$C_4$ alkyl, optionally substituted by a cyano, ($C_1$–$C_4$ alkyl)carbonyl, ($C_1$–$C_4$ alkoxy)carbonyl, di($C_1$–$C_4$ alkyl)aminocarbonyl, halogen or $C_1$–$C_4$ alkoxy;
        a phenyl or benzyl group, each of which can optionally bear 1 to 5 substituents selected from the group consisting of halogen, nitro, cyano, $C_1$–$C_4$ alkyl, $C_1$–$C_4$ alkoxy, $C_1$–$C_4$ haloalkyl, $C_1$–$C_4$ haloalkoxy and ($C_1$–$C_4$ alkoxy)carbonyl;
    a group CH$R_{11}$—$R_{15}$, wherein:
      $R_{11}$ is defined as above and
      $R_{15}$ is a heterocyclic group NC$_4R_{16}R_{17}$T, wherein each of $R_{16}$ and $R_{17}$, which are identical or different, is a hydrogen atom or a $C_1$–$C_3$ alkyl or ($C_1$–$C_3$ alkoxy) carbonyl group, and T is an oxygen or sulphur atom, or a carbonyl or N-$R_{18}$ group, wherein $R_{18}$ is a hydrogen atom or $C_1$–$C_4$ alkyl, formyl, ($C_1$–$C_4$ alkylcarbonyl or ($C_1$–$C_4$ alkoxy)carbonyl group;

h) a group —C(O)—X—$R_{19}$, wherein:
  X is an oxygen or sulphur atom,
  $R_{19}$ is:
    a $C_1$–$C_6$ alkyl group, optionally bearing a substituent selected from the group consisting of a halogen atom and a cyano group;
    a $C_3$–$C_6$ cycloalkyl group, optionally substituted by $C_1$–$C_3$ alkyl;
    a tri($C_1$–$C_4$ alkyl)silyl or phenylsulphonyl, optionally substituted by at least one halogen atom or $C_1$–$C_4$ alkyl;
    a ($C_1$–$C_4$ alkoxy)carbonyl or di($C_1$–$C_4$ alkyl) aminocarbonyl;
    a $C_2$–$C_6$ alkenyl or $C_2$–$C_6$ alkynyl group, each of which can optionally be substituted by phenyl, which can optionally bear 1 to 5 substituents selected from the group consisting of a halogen atom, a nitro group and a $C_1$–$C_4$ alkyl radical;
    a phenyl, benzyl, 2-pyridyl, 3-pyridyl or 4-pyridyl group, the nuclei of each of which can optionally bear 1 to 5 substituents selected from the group consisting of halogen, nitro, cyano, $C_1$–$C_4$ alkyl, $C_1$–$C_4$ alkoxy, $C_1$–$C_4$ haloalkyl, $C_1$–$C_4$ haloalkoxy, ($C_1$–$C_4$ alkyl)carbonyl, ($C_1$–$C_4$ alkoxy)carbonyl, $C_1$–$C_4$ alkylthio, $C_1$–$C_4$ alkylsulphinyl and $C_1$–$C_4$ alkylsulphonyl;
    a phenylalkyl group or a heterocyclylalkyl group, wherein the alkyl portion has 1 to 4 carbon atoms and the heterocyclyl portion is 2-pyridyl, 3-pyridyl, 4-pyridyl, 2-furyl, 3-furyl, 2-thienyl or 3-thienyl, the heterocyclyl nuclei optionally bearing 1 to 5 substituents selected from the group consisting of halogen, nitro, $C_1$–$C_4$ alkyl, $C_1$–$C_4$ alkoxy, $C_1$–$C_4$ haloalkyl, $C_1$–$C_4$ haloalkoxy, ($C_1$–$C_4$ alkyl)carbonyl, ($C_1$–$C_4$ alkoxy)carbonyl, $C_1$–$C_4$ alkylthio, $C_1$–$C_4$ alkylsulphinyl and $C_1$–$C_4$ alkylsulphonyl;

i) a group C(X)—N$R_{20}R_{21}$, in which:
  X is an oxygen or sulphur atom,
  each of $R_{20}$ and $R_{21}$ is:
    a hydrogen atom or a $C_1$–$C_4$ alkyl group, optionally bearing a substituent selected from the group consisting of halogen, cyano, ($C_1$–$C_4$ alkyl) carbonyl, ($C_1$–$C_4$ alkoxy)carbonyl and di($C_1$–$C_4$ alkyl)aminocarbonyl;
    a $C_3$–$C_6$ cycloalkyl group, optionally substituted by $C_1$–$C_3$ alkyl;
    a $C_3$–$C_6$ alkenyl or $C_3$–$C_6$ alkynyl group;
    a phenyl or benzyl group, the nuclei of each of which optionally bear 1 to 5 substituents selected from the group consisting of halogen, nitro, cyano, $C_1$–$C_4$ alkyl, $C_1$–$C_4$ alkoxy, $C_1$–$C_4$ haloalkyl, $C_1$–$C_4$ haloalkoxy, ($C_1$–$C_4$ alkyl)carbonyl, ($C_1$–$C_4$ alkoxy)carbonyl, $C_1$–$C_4$ alkylthio, $C_1$–$C_4$ alkylsulphinyl and $C_1$–$C_4$ alkylsulphonyl radical;
  $R_{20}$ and $R_{21}$ can additionally form, with the nitrogen atom to which they are joined, a ring having 6 atoms, 4 of which are optionally substituted carbon atoms and the fifth of which is a carbon atom or a heteroatom selected from the group consisting of oxygen, sulphur and nitrogen;

j) a group Si$R_{22}R_{23}R_{24}$, wherein each of $R_{22}$, $R_{23}$ and $R_{24}$, which are identical or different, is $C_1$–$C_4$ alkyl, phenyl or benzyl;

k) a group P(X)$R_{25}R_{26}$, wherein:
  X is an oxygen or sulphur atom,
  each of $R_{25}$ and $R_{26}$, which are identical or different, is $C_1$–$C_4$ alkyl, $C_1$–$C_4$ alkoxy, phenyl, phenoxy, benzyl or benzoxy;

with the proviso that when X is a hydrogen atom and R is a hydrogen atom, then Y is not a hydroxyl group or an alkoxy group; and with the further proviso that when X is a hydrogen atom, R is a methyl group and Y is a hydroxyl group, then Z is not a hydrogen atom or a methyl group.

2. The compound according to claim 1, having formula I.

3. The compound according to claim 1, wherein X is a chlorine or bromine atom.

4. The compound according to claim 1, wherein each of Y and Z is a hydrogen atom or a chlorine atom, provided that Y and Z cannot both be hydrogen.

5. The compound according to claim 3, wherein each of Y and Z is a hydrogen atom or a chlorine atom, provided that Y and Z cannot both be hydrogen.

6. The compound according to claim 1, wherein R is a hydrogen atom.

7. The compound according to claim 1, wherein R is a group $C(X)-R^{10}$ wherein X is oxygen or sulphur and $R_{10}$ is as defined in claim 1.

8. The compound according to claim 7, wherein R is ($C_1-C_3$ alkyl)carbonyl or phenylcarbonyl.

9. The compound according to claim 1, wherein R is a group $-C(O)-X-R_{19}$ wherein X is oxygen or sulphur and $R_{19}$ is as defined in claim 1.

10. The compound according to claim 9, wherein R is ($C_1-C_3$ alkoxy)carbonyl or phenoxycarbonyl.

11. The compound according to claim 1, having the formula

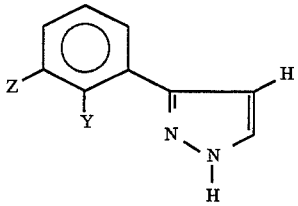

wherein:
Y is Cl and Z is Cl;
Y is Cl and Z is Br;
Y is Cl and Z is F;
Y is $CH_3$ and Z is Cl;
Y is F and Z is Cl;
Y is F and Z is F;
Y is $CH_3$ and Z is H;
Y is naphthyl and Z is naphthyl;
Y is $NO_2$ arid Z is Cl;
Y is $-OCH_2C_6H_5$ and Z is H;
Y is Cl and Z is $NO_2$;
Y is H and Z is Br; or
Y is $-CH_2Si(CH_3)_3$ and Z is Cl.

12. The compound according to claim 1, having the formula

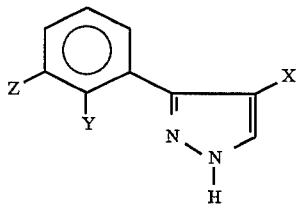

wherein:
Y is H, Z is Cl and X is Br;
Y is Cl Z is Cl and X is Br;
Y is $NO_2$, Z is Cl and X is Br;
Y is $CH_3$, Z is $CF_3$ and X is Cl;
Y is H, Z is $OCF_3$ and X is Cl;
Y is $OCH_3$, Z is Cl and X is Cl;
Y is Cl, Z is Br and X is Cl;
Y is H, Z is $CF_3$ and X is Cl;
Y is $C_2H_5$, Z is Cl and X is Cl;
Y is F, Z is Br and X is Cl;
Y is H, Z is CN and X is Cl;
Y is $CF_3$, Z is H and X is Cl;
Y is $SOCH_3$, Z is Cl and X is Cl;
Y is Cl, Z is F and X is Cl;
Y is $CH_3$, Z is Cl and X is Cl;
Y is F, Z is Cl and X is Cl;
Y is F, Z is $CF_3$ and X is Cl;
Y is F, Z is F and X is Cl;
Y is $CH_3$, Z is H and X is Cl;
Y is H, Z is F and X is Cl;
Y is $NO_2$, Z is Cl and X is Cl;
Y is $CH_3$, Z is $CH_3$ and X is Cl;
Y is H, Z is Cl and X is Cl;
Y is Cl, Z is $NO_2$ and X is Cl;
Y is H, Z is $NO_2$ and X is Cl;
Y is $NO_2$, Z is H and X is Cl;
Y is H, Z is Br and X is Cl;
Y is $CH_2Si(CH_3)_3$, Z is Cl and X is Cl;
Y is $NO_2$, Z is $SCH_3$ and X is Cl;
Y is $NO_2$, Z is $N(CH_3)_2$ and X is Cl;
Y is Br, Z is H and X is Cl;
Y is $NO_2$, Z is $CH_3$ and X is Cl; or
Y is $OC_2H_5$, Z is Cl and X is Cl.

13. The compound according to claim 1, which is selected from the group consisting of:
4-ethoxycarbonyl-3-(2-chlorophenyl)pyrazole,
4-methylthio-3-(2-nitro-3-chlorophenyl)pyrazole,
3-(3-bromophenyl)-4-(methylsulphonyl)pyrazole,
1-(thiocyanato)methyl- 4-chloro-3-(2-nitro-3-chlorophenyl)pyrazole,
1-acetyl-4-chloro-3-(2-methyl-3-chlorophenyl)-pyrazole, and
1-acetyl-4-chloro-3-(2-nitro-3-chlorophenyl)pyrazole.

14. The compound according to claim 1, having the formula

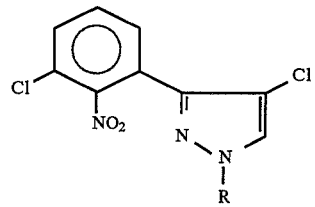

wherein R is $-C(O)OC_6H_5$, $-C(O)SC_2H_5$, $-CO_2C(CH_3)_2CO_2C_2H_5$, $-CO_2CHCH_2$, $-CO_2(p-NO_2-C_6H_4)$ or $-CO_2CH_2CHCl_2$.

15. A fungicidal composition comprising a fungicidally effective amount of a compound according to claim 1 and an agriculturally acceptable vehicle therefor.

16. The composition according to claim 15, further comprising an agriculturally acceptable surface-active agent.

* * * * *